(12) United States Patent
Glimberg et al.

(10) Patent No.: US 12,724,100 B2
(45) Date of Patent: Sep. 1, 2026

(54) METHOD AND APPARATUS FOR OPTICAL TRACKING OF MOTIONS OF A SUBJECT

(71) Applicant: TRACINNOVATIONS A/S, Ballerup (DK)

(72) Inventors: Stefan Lemvig Glimberg, Ballerup (DK); Claus Benjaminsen, Ballerup (DK)

(73) Assignee: TRACINNOVATIONS A/S, Ballerup (DK)

(*) Notice: Subject to any disclaimer, the term of this patent is extended or adjusted under 35 U.S.C. 154(b) by 150 days.

(21) Appl. No.: 18/721,276

(22) PCT Filed: Dec. 22, 2022

(86) PCT No.: PCT/DK2022/050309
§ 371 (c)(1),
(2) Date: Jun. 18, 2024

(87) PCT Pub. No.: WO2023/117026
PCT Pub. Date: Jun. 29, 2023

(65) Prior Publication Data

US 2025/0060443 A1 Feb. 20, 2025

(30) Foreign Application Priority Data

Dec. 22, 2021 (DK) .......................... PA 2021 70655

(51) Int. Cl.
*G01R 33/565* (2006.01)
*A61B 5/11* (2006.01)
*G01R 33/48* (2006.01)

(52) U.S. Cl.
CPC ...... *G01R 33/56509* (2013.01); *A61B 5/1113* (2013.01); *A61B 5/1126* (2013.01); *G01R 33/481* (2013.01)

(58) Field of Classification Search
None
See application file for complete search history.

(56) References Cited

U.S. PATENT DOCUMENTS 5,687,725 A * 11/1997 Wendt .................. G01R 33/285 324/309
7,495,438 B2 * 2/2009 Prince .................... A61B 5/055 324/309

(Continued)

OTHER PUBLICATIONS

Jain et al.: "Measuring light transport properties using speckle patterns as structured illumination", Scientific Reports (2019) 9:11157.

(Continued)

*Primary Examiner* — Jermele M Hollington
(74) *Attorney, Agent, or Firm* — DUANE MORRIS LLP; Gregory M. Lefkowitz; Daniel J. Tarr

(57) ABSTRACT

A method of and an apparatus for motion tracking of a subject located in a scanner are presented. The method comprises generating a baseline 3D surface representation of a surface region of the subject at a first point of time (T(0)); generating a subsequent 3D surface representation of the surface region of the subject at a subsequent point of time (T(s)); determining a best-fit registration of the subsequent 3D surface representation with at least one constraint relative to the baseline 3D surface representation and determining at least one motion tracking parameter. The method may include selecting at least one virtual feature and associating the at least one virtual feature to the baseline 3D surface representation, wherein the constraint comprises a restriction of at least one parameter of the at least one virtual feature associated to the best-fit subsequent 3D surface representation relative to the at least one parameter of the at least one virtual feature associated to the baseline 3D surface representation.

21 Claims, 12 Drawing Sheets

(56) References Cited

U.S. PATENT DOCUMENTS

| | | | | |
|---|---|---|---|---|
| 8,463,006 | B2 * | 6/2013 | Prokoski | G06T 7/0012 382/128 |
| 8,494,227 | B2 * | 7/2013 | Prokoski | G06T 7/0012 382/270 |
| 10,912,461 | B2 | 2/2021 | Olesen | |
| 2005/0054910 | A1 | 3/2005 | Tremblay | |
| 2013/0093866 | A1 | 4/2013 | Ohlhues | |
| 2014/0073904 | A1 | 3/2014 | Biber | |
| 2014/0093160 | A1 | 4/2014 | Porikli | |
| 2015/0139515 | A1 | 5/2015 | Smith | |
| 2017/0032538 | A1 | 2/2017 | Ernst | |
| 2017/0196529 | A1 | 7/2017 | Lin | |
| 2018/0070904 | A1 | 3/2018 | Yu | |
| 2020/0146554 | A1 | 5/2020 | Olesen | |
| 2020/0405179 | A1 | 12/2020 | Kirsch | |
| 2021/0046329 | A1 | 2/2021 | Lachaine | |
| 2021/0325501 | A1 | 10/2021 | Kroeker | |
| 2022/0196832 | A1 * | 6/2022 | Gollakota | G01S 7/52095 |

OTHER PUBLICATIONS

Larsson: “Morph targets and bone rigging for 3D facial animation”, Uppsala University, Jun. 2017.

Zizka et al. “SpeckleSense: Fast, Precise, Low-cost and Compact Motion Sensing using Laser Speckle” UIST'11, Oct. 16-19, 2011, Santa Barbara, CA, USA. DOI: 10.1145/2047196.2047261.

Reilly et al. “Adaptive Noncontact Gesture-Based System for Augmentative Communication” IEEE Transactions on Rehabilitation Engineering, vol. 7, No. 2, Jun. 1999.

De Aguiar, E., et al. “Marker-less Deformable Mesh Tracking for Human Shape and Motion Capture”, 2007 IEEE Conference on Computer Vision and Pattern Recognition, Minneapolis.

Tchvialeva et al.: “Optical discrimination of surface reflection from volume backscattering in specle contrast for skin roughness measurements”, Proceedings of SPIE, Feb. 2009, vol. 7161.

Ilg et al.: “Reconstruction of rigid body models from motion distorted laser range data using optical flow”, 2014 IEEE International Conference on Robotics and Automation (ICRA), May 31, 2014, ISBN: 978-1-4799-3685-4.

Olesen, O.V., et al., “Motion Tracking in Narrow Spaces: A Structured Light Approach”, Sep. 20, 2010, 18th International Conference, Austin, TX, USA, Sep. 24-27, 2015; [Lecture Notes in Computer Science; Lect.Notes Computer], Springer, Berlin, Heidelberg, pp. 253-260, XP047463062, ISBN: 978-3-540-74549-5, * p. 254-p. 256 *.

* cited by examiner

Anatomically plausible
41
44

Anatomically implausible
45
44

46
41
44

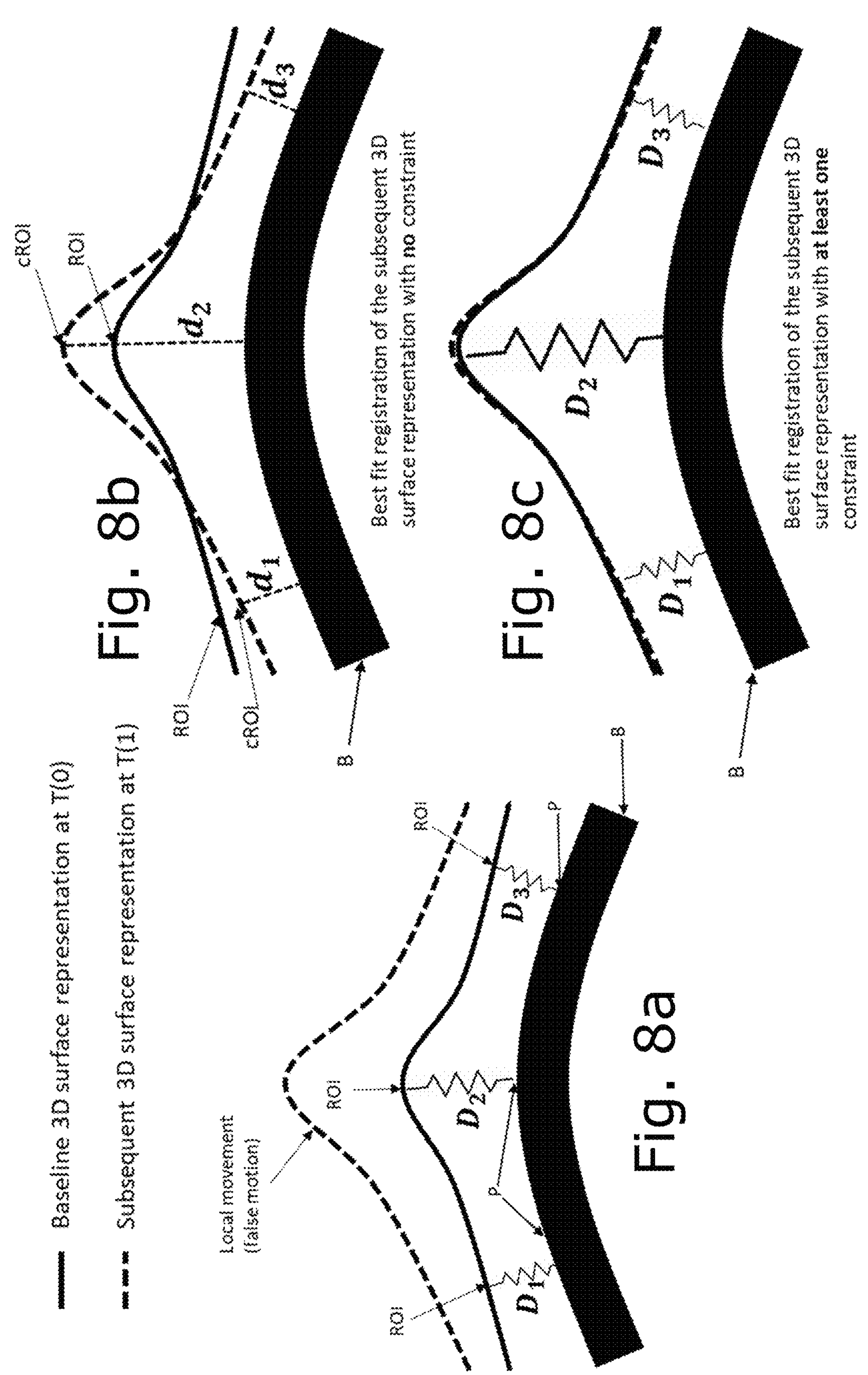
Baseline 3D surface representation at T(0)
Subsequent 3D surface representation at T(1)
Fig. 8a
Local movement (false motion)
ROI
ROI
ROI
ROI
$D_1$
$D_2$
$D_3$
P
P
B
Fig. 8b
cROI
ROI
ROI
cROI
$d_1$
$d_2$
$d_3$
B
Best fit registration of the subsequent 3D surface representation with no constraint
Fig. 8c
$D_1$
$D_2$
$D_3$
B
Best fit registration of the subsequent 3D surface representation with at least one constraint

METHOD AND APPARATUS FOR OPTICAL TRACKING OF MOTIONS OF A SUBJECT

CROSS-REFERENCE TO RELATED APPLICATIONS

This application is a § 371 national stage entry of International Application No. PCT/DK2022/050309, filed on Dec. 22, 2022, which claims priority to Danish Patent Application No. 2021 70655, filed on Dec. 22, 2021, the entire contents of which are incorporated herein by reference.

TECHNICAL FIELD

The present invention relates to a method and an apparatus for motion tracking of a subject located in a scanner, such as in a bore of a medical scanner, such as in magnetic resonance imaging (MRI) scanner or positron emission tomography (PET) scanner or a combined MRI/PET scanner.

BACKGROUND

Over the last decade, numerous methods for motion tracking of a subject during a medical scanning have been developed in particular for medical brain scanning: however, head motion during scanning pertains to be a significant problem causing artefacts and significantly reducing image quality. Also for scanning of other body parts of a subject, such as heart scanning or lung scanning, undesired motions of the subject during the scanning procedure may severely reduce the scanning quality.

Known methods include external tracking systems as well as image based motion tracking. Many external tracking systems use markers attached to the subjects head. This potentially introduces errors and complicates the process of preparing the subject for the scan and therefore reduces the usability in clinical practice. Generally, the known tracking system tracks a surface area of an object during a scanning procedure and apply detected motions for correcting the medical scanning images or to identify if a motion exceeds a threshold that indicates that the medical scanning result may be unacceptable. The operator may then restart the scanning procedure thereby saving time and reducing cost. However, often the tracking system detects “false motions” which may result in a poor or even a worsening of the “corrected” medical scanning images and/or in unnecessary termination of a scanning procedure.

U.S. Pat. No. 20,201,46554 describes a scanning monitoring apparatus for medical imaging, comprising a controller unit and a display, wherein the controller unit during a scanning session is configured to obtain tracking data of a subject in a medical scanner, obtain scanner data indicative of operating parameters of the medical scanner; determine an output of a verification function based on the tracking data and the scanner data; and control the scanning monitoring apparatus according to the output of the verification function. A notification signal may be provided if the output is indicative of an erroneous scanning.

EP3896641 describes a method for correcting a movement of an object occurring during an MR image acquisition in which the MR signals of the object are detected. The described method has the purpose of helping to discriminate a wrongly detected motion from an actual motion of the object under examination as it can be determined whether a detected motion of a marker located on the object is an actual motion, which can be carried out by the object. The method comprises determining a motion model, which describes the possible movements of the object based on a model function having a defined number of degrees of freedom the object is able to use for the movement. Motions of the marker on the object is detected with a motion sensor. A description of the motion model and the motion of the marker is determined in a common coordinate system and a first motion of the object is determined in the common coordinate system using the description of the motion model, wherein this first motion is the motion that best matches the determined motion of the marker in the common coordinate system using the defined number of degrees of freedom.

Whereas this system may reduce the detection of some “false motions”, it requires a generation of a motion model for each respective objects. Further, there is a high risk that some motions, such as unexpected or uncommon motions, may incorrectly be determined to be false. In addition, the method described is not adapted for detecting false motions, which do not exceed the motion model.

DISCLOSURE OF THE INVENTION

An object of the invention is to provide a method and an apparatus for motion tracking of a subject located in a scanner, such as in a scanner bore, which alleviates at least a part of the problems discussed above.

In an embodiment, it is an object to provide a method, which method ensures an increased motion tracking quality.

In an embodiment, it is an object to provide an apparatus, which is capable of performing real time motion tracking of high quality.

These and other objects have been solved by the invention or embodiments thereof as defined in the claims and/or as described herein below.

It has been found that the invention or embodiments thereof have a number of additional advantages, which will be clear to the skilled person from the following description.

According to the invention, it has been found that surprising high quality tracking quality may be obtained by providing a suppressing of false motion detection as provided by a method and an apparatus comprising the features as defined in the claims and as described herein.

Specifically it has been found that movement of the surface region may not entirely represent the motions that are desired to track. By suppressing certain detected movements of the surface region—specifically certain local detected movements of the surface region a much more accurate motion tracking may be obtained. The invention presents a method and a system, which may be applied systematically to suppress such detected movement of the surface region that does not entirely represent the motion that are desired to track. Such movements are also referred to a “false motion”.

Thus in an embodiment where certain locations of the surface under tracking tends to local movement, which does not reflect the overall movement of the body part in question i.e. the motion that is to be tracked, the method and the system of the invention may effectively be applied for suppressing such false motions in the motion tracking of the subject located in the scanner. Such false motions may e.g. be movements caused by tension of a muscle, blinking, movements of mouth region etc. depending on the body part to be subjected to the motion tracking.

It has been found that, in addition to detection of false motion also detection errors may occur e.g. due to movements (false or not) providing shadow area, changed incidence and/or reflection angle or any other optical phenomena, apparatus error and/or calibration errors. It has been found that the method and the apparatus of the invention may provide a desired and effective suppression of such detection errors.

Additional benefits and applications will be clear to the skilled person from the description and examples below.

The method of motion tracking of a subject located in a scanner bore of the invention comprises generating a baseline 3D surface representation of a surface region of the subject at a first point of time (T(0)).

generating a subsequent 3D surface representation of the surface region of the subject at a subsequent point of time (T(s)), determining a best-fit registration of the subsequent 3D surface representation with at least one constraint relative to the baseline 3D surface representation, determining at least one motion tracking parameter.

By applying at least one constraint in the determination of the best-fit registration of the subsequent 3D surface relative to the baseline 3D surface representation, detection of false motions and/or detection errors may be suppressed, thereby providing motion tracking with an improved accuracy and quality.

The method may comprise a computer implemented method.

The term "subject" is herein used to mean any subject capable of moving, preferably a living subject, preferably a mammal such as a human being.

Often only a part of the subject is subjected to the motion tracking, such part is herein referred to as a body part. Advantageously, the body part comprises a body portion subjected to medical scanning in the scanner. Advantageously, the body portion is an internal portion of the body part, such as a brain portion of a head, a joint portion of a knee, a heart or lung portion of a chest and etc.

The surface region of the subject may advantageously be a surface region of the body part in question. The surface region is advantageously selected to be a characteristic surface area, such as a surface area with a curvature and/or a color and/or structure variation, such as a surface area comprising the nasal bridge where the body part comprises a head or a surface area comprising a nipple where the body part comprises a part of the chest.

The motion tracking may advantageously be a markerless scanning i.e. without adding any markings on or at the subject or the body part of the subject.

However, in some situations it may be beneficial to apply a marking, such as a marling onto the skin of the body part e.g. to mark the location of the body portion to be scanned. Using a marking may for example be beneficial where the surface area of the body part located above the body portion to be scanned is relatively un-curved and evenly in structure and/or color.

The scanner is advantageously a medical scanner such as an X-ray scanner a MRI scanner, a CT scanner, a PET scanner, an ultrasound scanner, Bone densitometry (DXA) and/or any combinations thereof.

The subject or at least the body part of the subject is located in the scanner by being located in the scanner target space, i.e. the area where the scanner may perform scanning. The subject or at least the body part of the subject is advantageously located in a scanner bore of the scanner.

The motion tracking may advantageously be performed in real time.

The phrase "real time" is herein used to mean that the time from generating the subsequent 3D surface representation of the surface region to determining the at least one motion tracking parameter is 1 second or less, such as 0.1 second or less, such as 0.01 second or less.

Where the motion tracking is performed in real time, one or more scanning parameter may be adjusted, preferably in real time, in dependence of the motion tracking in real time, such as adjusting the magnetic field in MRI scanning, the radio waves and/or the sequences thereof an well as optionally performing reacquisition of fraction(s) of a scanning procedure. Due to the accuracy of the tracking and due to the suppression of false motions and/or scanning errors, it may often be sufficient to perform reacquisition of fraction(s) of a scanning procedure of relatively short fractions, e.g. up to 5 minutes or less, such as up to 1 minute, such as 1-30 seconds, such as 2 to 10 seconds to obtain a high quality scanning. Thereby an entire scan and/or an image acquisition time for acquire data for an image need not be repeated, which ensures that the scanning procedure may be performed relatively fast, while at the same time ensuring a very high scanning quality.

Where the motion tracking indicates a movement beyond what is correctable, the scanning may in an embodiment be stop or be stopped by an operator, e.g. for restarting the entire scanning procedure. Thereby both time and cost may be saved and the patient need not be subjected to rescanning at a later stage, since the scanning error is immediately observed.

In an embodiment, the motion tracking may advantageously be performed with a delay, which means that the time from generating the subsequent 3D surface representation of the surface region to determining the at least one motion tracking parameter is longer than 1 second, such as longer than 5 seconds or even longer. The motion tracking with a delay may for example be applied for examination of movements, such as movement patterns for selecting suitable constraints as explained further below or for determining accuracy of the scanning result and/or for after corrections of scanning results. For example in bone densitometry, several, e.g. 2, 3 or more scans are often taken and the result may be taken as the average result. Using the method of the invention, it may be determined if undesired movements has occurred during scanning of any of the scan and if so such scans may be deemed to have scanning error(s) and may be discarded. For example, in that embodiment the motion tracking may or may not be in real time.

The term "computer system" is herein used to mean one single computer or a plurality of computers in data connection, wireless, by wire and/or via the internet, wherein the term "computer" means a machine or device is capable of processing data at least partly based on instructions provided by a software and/or hardware program. It has the ability to accept data (input), process it, and then produce outputs.

The term "configured for" are used to mean "programmed for" and/or taught e.g. by machine learning which may be a supervised or non-supervised machine learning.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Throughout the description or claims, the singular encompasses the plural and the plural encompasses the singular unless otherwise specified or required by the context.

The "an embodiment" should be interpreted to include examples of the invention comprising the feature(s) of the mentioned embodiment.

The term "about" is generally used to include what is within measurement uncertainties. When used in ranges the term "about" should herein be taken to mean that what is within measurement uncertainties is included in the range.

The phrase "region of interests" (ROI) is herein used to mean a sub-region or a set of sub-regions of the baseline 3D surface representation corresponding to actual sub-region(s) of the surface region or corresponding to actual sub-region(s) of a portion of the subject at least partly correlated with actual sub-region(s) of the surface region. The term "substantially" should herein be taken to mean that ordinary product variances and tolerances are comprised. All features of the invention and embodiments of the invention as described herein, including ranges and preferred ranges, may be combined in various ways within the scope of the invention, unless there are specific reasons not to combine such features.

The generation of the baseline 3D surface representation and the subsequent 3D surface representation of the surface region is advantageously performed optically by detecting light reflections from the surface region. The baseline 3D surface representation is acquired at the time T(0), which may be any time prior to the time T(s) of acquisition of the subsequent 3D surface representation of the surface region. Advantageously, the method comprises repeatedly generation of subsequent 3D surface representations of the surface region and determination of at least one motion tracking parameter, wherein the applied baseline 3D surface representation may be the same or differ for the respective subsequent 3D surface representation of the surface region. In an embodiment, a first baseline 3D surface representation is maintained as the same for a plurality, such as all subsequent 3D surface representation of the surface region.

In an embodiment, the first baseline 3D surface representation is replaced by a second baseline 3D surface representation e.g. after a selected scanning time, at a selected stage of the scanning and/or if the first baseline 3D surface representation is suspected of comprising scanning error(s).

In an embodiment, the generation of the baseline 3D surface representation comprises generating a single 3D surface representation of the surface region and apply this single 3D surface representation of the surface region as the baseline 3D surface representation.

The generation of the baseline 3D surface representation may comprise one or more filtered images, such a two or more images acquired over time e.g. over up to 30 seconds, such as up to 10 seconds, e.g. at a frame rate of 1 Hz or more e.g. a frame rate of up to—1000 Hz, such as 2-100 Hz.

In an embodiment, the generation of the baseline 3D surface representation comprises generating a plurality of 3D surface representation of the surface region and provide an average or median of the plurality of 3D surface representation of the surface region and apply this average/medial 3D surface representation of the surface region as the baseline 3D surface representation. The average or median of the plurality of 3D surface representation of the surface region may be determined as a point by point average/median, where the respective points may be respective pixels or groups of pixels or light beams depending on the required/desired resolution.

In an embodiment, the generation of the baseline 3D surface representation comprises generating a plurality of 3D surface representation of the surface region until a number, such as 2 or more e.g. 3 to 10 of the generated surface representation of the surface region are identical within a selected threshold and applying this identical surface representation as the baseline 3D surface representation.

The at least one constraint advantageously comprises a relative restriction. Thus it has been found that the false motion and/or detection errors are seldom isolated from actual movement, i.e. the may be related to and/or partly caused by actual movements. Thus, in an embodiment the constraint comprises a relative restriction, wherein the relative restriction may be a function of a difference between respective locations of the baseline 3D surface representation and corresponding respective locations of the subsequent 3D surface representation. The constraint may be applied as a restriction in spatial distance between respective locations of the baseline 3D surface representation and corresponding respective locations of the subsequent 3D surface representation, wherein a respective location of the baseline 3D surface representation and corresponding respective location of the subsequent 3D surface representation are location that homographically are matching, i.e. locations that represents matching points of the surface region.

In an embodiment, the method comprises selecting at least one virtual feature and associating the at least one virtual feature to a ROI (region of interest) of the baseline 3D surface representation, wherein the constraint comprises a restriction of change of at least one parameter of the at least one virtual feature associated to a corresponding ROI of the best-fit subsequent 3D surface representation relative to the at least one parameter of the at least one virtual feature associated to the ROI of the baseline 3D surface representation.

The at least one virtual feature may advantageously have a spatial location (i.e. in the image be located) relative to the ROI and/or the corresponding ROI. For example the distance between the virtual feature and the ROI of the baseline 3D surface representation respectively the corresponding ROI of the subsequent 3D surface representation may be a parameter of the constraint i.e. the constraint may comprise a restriction of change of the distance from the distance between the virtual feature and the ROI of the baseline 3D surface representation to the distance between the virtual feature and the ROI of the subsequent 3D surface representation, to arrive at a suppressed change of distance from the distance between the virtual feature and the ROI of the baseline 3D surface representation to the distance between the virtual feature and the ROI of the best-fit subsequent 3D surface representation.

The parameter that may be restricted is also referred to a parameter of the constraint e.g. the parameter of the constraint may be the distance between the ROI/corresponding ROI.

The virtual feature may advantageously be a virtual feature, which have a spatial location at a spatial distance to the 3D surface representation of the surface region. The at least one virtual features may for example comprise at least one of a virtual point, a virtual cloud of points (in 2D or 3D), virtual volume, a virtual area, a virtual line, a virtual bone structure and/or any combination comprising one or more of the mentioned virtual features.

The association to the baseline 3D surface representation may comprise an association to a spatial location, an orientation, an extent or a combination of one or more to a point, an area or a line of the baseline 3D surface representation.

Advantageously, the association to the baseline 3D surface representation may comprise an association to the ROI, such as a spatial location of the ROI, an orientation of the ROI, an extent or a combination of one or more to a point of the ROI, an area or a line of the ROI of the baseline 3D surface representation.

Advantageously, the at least one parameter comprises a location parameter, an orientation parameter, an extent parameter and/or a combination comprising at least one of the mentioned parameters of the at least one virtual features.

In an embodiment, the at least one parameter comprises a location parameter, a distance parameter, an orientation parameter and/or two or more virtual features relative to another or any combination comprising at least one of the mentioned parameters of the virtual feature(s) associated to the ROI of the baseline 3D surface representation.

The constraint of the at least one parameter may advantageously comprise a linear restriction, a logarithmic restriction, an exponential restriction, a maximal restriction and/or a conditioned restriction comprising one or more of the before mentioned conditioned based on the difference in parameter (e.g. baseline parameter) from the baseline 3D surface representation to the unconstrained parameter of the subsequent 3D surface representation.

Thereby false motions and/or detection errors will be suppressed. The degree of suppression depends on the selection of the one or more selected constraints.

In an embodiment, the constraint of the at least one parameter comprises a conditioned restriction comprising one or more of the before mentioned, wherein a condition of the conditioned restriction is based on an unconstrained difference of the at least one parameter of the at least one virtual feature associated to the ROI of the baseline 3D surface representation relative to the at least one virtual feature associated to a corresponding ROI of the subsequent 3D surface representation.

For example, if a subject performs movements comprising blinking or even squeezing his eyes together during a brain scanning where the surface region comprises the nasal and eye region, one or more virtual features may be spatially located at a location corresponding to the inside of the head and be associated to the portion (e.g. the ROI) of the baseline 3D surface representation representing the part of the surface region provided by soft tissue such as the eye region. The constraint may for example comprise a spatial distance restriction, providing a relative restriction to the distance between the virtual feature(s) and its/their association to the corresponding ROI of the subsequent 3D surface representation compared to the distance between the virtual feature(s) and its/their association to ROI of the baseline 3D surface representation. Thereby false motions, i.e. movements of the eye region not relating to any movements of the body portion under scanning, may be suppressed, whereas other movements may be registered with the best-fit registration of the subsequent 3D surface representation with at least one constraint relative to the baseline 3D surface representation.

In an embodiment, the ROI is a sub-region or a set of sub-regions of the baseline 3D surface representation corresponding to actual sub-region(s) of the surface region or corresponding to actual sub-region(s) of a portion of the subject at least partly correlated with actual sub-region(s) of the surface region.

A set of sub-regions may for example comprises two or more points, lines, curves, areas of the baseline 3D surface representation corresponding to two or more points, lines, curves, areas of the actual surface region.

In an embodiment, the ROI comprises at least one sub-region of the baseline 3D surface representation and the corresponding ROI is/are sub-region(s) of the subsequent 3D surface representation and/or sub-region(s) of the best-fit subsequent 3D surface representation corresponding to actual sub-region(s) corresponding to the ROI of the baseline 3D surface representation.

The ROI may conveniently have a location at the baseline 3D surface representation wherein the location of the ROI corresponds to the location of the corresponding ROI at the actual sub-region(s) of the surface region.

The ROI may in an embodiment, be characterized by at least one of a spatial location, an orientation, a shape, an extend, an area or a combination comprising one or more of the mentioned characteristics, wherein each of virtual feature may be associated to the baseline 3D surface representation by an association comprising one or more of the mentioned characteristics.

The ROI may for example comprise a 0D sub-region, such as a point; a 1D sub-region, such as a line; a 2D sub-region, such as a surface area; a 3D sub-region, such as a volume or any combinations thereof.

To ensure a sufficient brightness of the reflected light, it is desired to illuminate the surface region. Thereby also the angle of light incidence and type and structure of the light may be selected to provide a desired quality of the motion tracking.

In an embodiment, the generation of respectively the baseline 3D surface representation and the subsequent 3D surface representation does not require any specific illumination and projecting of light onto the surface region may not be required and incident light may suffice.

In an embodiment, the generation of respectively the baseline 3D surface representation and the subsequent 3D surface representation comprises projecting light from a projector arrangement towards the surface region of the subject and detecting reflections at a detection location of the projected light.

In an embodiment, the constraint comprises providing that the at least one virtual feature associated to the best-fit registered subsequent 3D surface representation has been transformed compared to what it would have been without the at least one constraint. Thereby at least one false motion and/or at least one detection error has been suppressed in the best-fit registration of the subsequent 3D surface representation. Advantageously, the transformed virtual feature(s) comprises a transformation of the at least one parameter (also referred to as "transformed parameter"), wherein the transformation comprises at least one restriction of the at least one parameter.

The constraint may in principle have any number of degree of freedom. The Term "degree of freedom" is in the following referred to a DOF.

In an embodiment, the constraint has at least one DOF, preferably selected from a translation axis and a rotation axis. Optionally the constraint is restricting in only one translation direction along a translation axis. In an embodiment, the at least one DOF comprises a DOF of the at least one parameter, such as a DOF of the transformation of the at least one parameter.

The constraint may advantageously be an X DOF constraint, wherein X is an integer from 1-6. Preferably, X is an integer from 1-3, such as a 1 DOF constraint, a 2 DOF constraint or a 3 DOF constraint, wherein the constraint is or comprises 1, 2 or 3 translation axis.

Thus, a constraint may have one or more weight attributes i.e. one for each DOF, wherein at least one of the weight attributes provides a restriction. Where the constraint has only one DOF it may have only one weight attribute.

For certain motion tracking's, specifically where a substantial number of false motions and/or detection errors may be expected, it may be desired that the constraint comprises 2 or more DOF. However, the more DOF of a constraint, the more complex may the determination be. An alternative too many DOF's of a constraint may therefore be to raise the number of constraints.

Advantageously, the constraint is associated to a weight attribute representing a weight value of the constraint, preferably, the constraint is associated to a set of weight attributes comprising at least 2 weight attributes. Advantageously, the constraint is associated to a weight attribute for each DOF.

A weight attribute means herein the weight of the at least one parameter of the at least one virtual feature associated to the best-fit subsequent 3D surface representation relative to the at least one parameter of the at least one virtual feature associated to the baseline 3D surface representation.

The virtual feature may be associated to the best-fit subsequent 3D surface representation by being associated to the corresponding ROI of the best-fit subsequent 3D surface representation.

The virtual feature may be associated to the baseline 3D surface by being associated to the ROI of the baseline 3D surface representation.

For example, where the parameter comprises a distance parameter providing a restriction selected from for example a linear or a logarithmic restriction, the weight attribute represent the weight of the restriction i.e. to which degree the restriction should be applied.

Advantageously, the set of weight attributes comprises a weight attribute for each of 2 or more specific DOF representing the weight of the constraint of the specific DOF. In an embodiment, the constraint is a 6 DOF constraint and wherein the set of weight attributes comprises a weight attribute for each of the respective DOF of the 6 DOF constraint.

The values of the respective weight attributes of the set of weight attributes may be equal or it may comprise weight attributes that differs from each other in value. For example, the value of the respective weight attributes of the set of weight attributes may be selected independently of each other.

Advantageously, the at least one virtual feature associated to the baseline 3D surface representation has a baseline parameter. The value of the respective weight attributes of the set of weight attributes may conveniently be selected in dependence of the at least one virtual feature and its baseline parameter, such as a baseline location parameter, a baseline orientation parameter, a baseline extent parameter and/or a baseline distance parameter.

For example in an embodiment, the virtual feature is a virtual point located in the head of a subject—e.g. in a center of the head and the parameter of the virtual feature associated to the baseline 3D surface representation is a distance parameter i.e. the baseline parameter is the distance between the virtual feature and the ROI of the baseline 3D surface representation to which the virtual feature is associated e.g. to a point of association to the baseline 3D surface representation. The constraint may then comprise a restriction of the distance corresponding virtual feature of the subsequent 3D surface representation of the surface region to the associated corresponding ROI comprising the point of association of the subsequent 3D surface representation of the surface region and the weight of the DOF of the constraint may be selected in dependence of the virtual feature and the baseline parameter.

Advantageously, the baseline parameter is the at least one parameter of said at least one virtual feature associated to the ROI of the baseline 3D surface representation.

The weight of the respective weight attributes may be selected in several ways. For example, the weight attribute(s) may be selected arbitrary by an operator e.g. based on experience or by a try and error method. However, for several scanning types such arbitrary selection is not desired or appropriate. For, optimizing the weight attribute(s) it is desired that such weight attribute(s) is/are derived from a modeling.

In an embodiment, the weight of the respective weight attributes of the set of weight attributes are derived from a modelling of expected movements of the at least one virtual features preferably by movement of an anatomical model of a body part of the subject comprising the surface region. By deriving the weight attributes by such a modeling procedure, a very accurate correlation between movements of the virtual point relative to movements of the body portion, which is target for the scanning and movements of the surface region may be obtained and thereby optimized weight attributes may conveniently be obtained. Advantageously, the weight of the respective weight attributes of the set of weight attributes are derived from a modelling of expected movements of the at least one virtual features relative to its/their baseline parameter(s) by movement of an anatomical model of the body part of the subject comprising the surface region. In an embodiment, the body part of the subject comprises the surface region comprises a human head.

In an embodiment, the value of the respective weight attributes of the set of weight attributes may be dynamically adjusted. For example the value of the respective weight attributes of the set of weight attributes may be dynamically adjusted in dependence of the subsequent 3D surface representation of the surface region, such as in dependence of the noise of the subsequent 3D surface representation of the surface region. For example in an embodiment, the value of at least one of the weight attributes may be increased with increased noise, thereby increasing the suppression of potential detection errors which may contribute in the formation of the noise.

In an embodiment, it may be desired to determining the unconstraint parameter of the at least one virtual feature associated to corresponding ROI of the subsequent 3D surface representation of the surface region of the subject at the subsequent time, wherein a movement of a body part of the subject comprising the surface region between the first point in time and the subsequent point of time provides that the unconstraint parameter differs from the transformed parameter i.e. the parameter after the restriction(s) of the constraint. The unconstrained parameter is the parameter i.e. the distance, the orientation etc. of the virtual feature associated to the corresponding ROI of the subsequent 3D surface representation of the surface region without any constraint. Thereby, by comparing the unconstraint parameter with the transformed parameter, the level of suppression may be observed. This may for example be applied as a control of the operation of the method and the system.

Where the parameter is a distance parameter the transformed parameter may conveniently be closer to the baseline parameter than the unconstraint parameter.

The 3D surface representations may advantageously be acquired using an acquisition arrangement. The acquisition arrangement may for example be as described in U.S. Pat. No. 10,912,461 or in EP 2,547,255. Thus, in an embodiment, the acquisition arrangement comprises a fiber bundle with a first end for collecting reflected light from the surface region and a second end for delivering the light propagated in the fibers of the fiber bundle to a detector/camera. In an embodiment, the acquisition arrangement comprises a borescope. In an embodiment, the acquisition arrangement comprises one or more 2D and/or 3D readers such as one or more detectors/cameras e.g. including at least one mono or stereo camera comprising an array of pixel sensors. Each of the pixel sensors preferably comprises a photodetector, such as an avalanche photodiode (APD), a photomultiplier or a metal-semiconductor-metal photodetector (MSM photodetector). The pixel sensor may advantageously include one or more active pixel sensors (APS). Each pixel sensor may comprise an amplifier. The associated detector may advantageously comprise at least about 1 kilo pixels, such as at least about 1 Mega pixels. In an embodiment the acquisition arrangement a charge-coupled device (CDD) image sensor, or a complementary metal-oxide semiconductor (CMOS) image sensor.

Advantageously, the at least one virtual feature as associated to the baseline 3D surface representation is located at the surface region or at a distance further from the surface region than an acquisition arrangement acquiring reflected light from the surface region for generating the respective surface representations.

Advantageously, the at least one virtual feature as associated to the baseline 3D surface representation is located between the surface region and a bearing supporting the subject, such as a scanner bed. Preferably the at least one virtual feature as associated to the baseline 3D surface representation is located in a middle region between the surface region and the bearing, wherein the middle region may extend from 40% of a bearing to surface region distance to 75% of the bearing to surface region distance, such as from 50% to 65% of the bearing to surface region distance. The bearing to surface distance may adequately be the distance between the surface region and the bearing determined from the acquisition arrangement, e.g. from the point of the acquisition arrangement which is closest to the surface region and/or from a point of collection of reflected light of the acquisition arrangement.

In an embodiment, the surface region comprises a surface region of a body part of the subject, wherein the virtual feature comprises a virtual point, a virtual line or a virtual bone structure, which at least at the first point of time (i.e. when acquiring reflected light for the generation of the baseline 3D surface representation at T(0)) is located inside a volume of the body part and wherein the parameter comprises a location parameter, an orientation parameter and/or a distance parameter. Preferably, the body part comprises a human head, and the surface region comprises at least a portion of a curvature of a nasal bridge of the subject.

In an embodiment, the virtual feature, such as a virtual point is located inside the body part e.g. inside the body portion which is target for the scanning. The virtual feature may for example be located at a distance—determined as minimum distance at the time T(0)—from the surface region, which is at least 1 cm, such as at least 2 cm, such as at least 3 cm, such as at least 4 cm, such as at least 5 cm determined from the location of the acquisition arrangement.

In an embodiment, the body part comprises a bone structure and where the bone structure comprises a surface area contributing to shaping the surface region of the subject in the scanner and the method comprises selecting a plurality of virtual features (e.g. virtual points) located at the bone structure surface area and wherein each of the virtual features are associated to an ROI e.g. a location of the baseline 3D surface representation at respective location corresponding to the shortest distance between virtual feature and the (ROI) location of the baseline 3D surface representation and/or where a distance line between virtual feature and associated ROI/location of the baseline 3D surface representation is normal to the bone structure surface area.

In this embodiment the constraint may advantageously comprise a restriction of the length (which is thus the restricted parameter) of each of the distance line. The restriction of the respective length of the distance lines may advantageously be such that at least two of the restrictions differs. The distance lines may be considered as extension/compression springs, which may have a outset length determined in respect of the baseline 3D surface representation and wherein the change of spring length is restricted by a value k, which may be a constant or a function and where k may differ from one extension/compression spring to another extension/compression spring. E.g. where k is 0.1 and the change of the distance line in respect of the subsequent 3D surface representation of the surface region without constraint is a mm, the resulting length of the distance line (i.e. the resulting length of the constant/compression spring with the k value 0.1) will be 0.1*a.

In an embodiment, the k value is a function, such as a function, which may be dependent of the size of the change of the distance line in respect of the subsequent 3D surface representation of the surface region without constraint or a function, which may be dependent of another distance line in respect of the subsequent 3D surface representation of the surface region without constraint.

In an embodiment, the body part is a part of the chest comprising the heart, which comprises the body portion that is target for the scanning and the virtual feature, such as a virtual line is located partly or fully inside the body portion.

In an embodiment, the body part comprises a joint, such as a knee, an elbow, an ankle, a wrist or a shoulder. The virtual feature(s), such as two or more points may conveniently be located partly or fully inside the knee, elbow, ankle, wrist or shoulder.

In an embodiment, the surface region comprises a surface region of a body part of the subject, wherein the virtual feature comprises a virtual volume and/or a virtual area, which at the first point of time is located at the surface region and/or at least partly inside a volume of the body part and wherein the parameter comprises a location parameter, an orientation parameter and/or an extend parameter. Preferably, the body part comprises a human head, and the surface region comprises at least a portion of a curvature of a nasal bridge of the subject.

In an embodiment, the method comprises selecting the at least one virtual feature with a feature location at T(0), by providing estimated movements of the subject during a scanning section and selecting the virtual feature with feature location at T(0), which is subjected to less constraint parameter changes than other virtual features of the subject and/or to be a virtual feature with a feature location subjected to parameter changes below a preselected level. The provision of estimated movements of the subject during a scanning procedure may preferably be provided from determined movements of subjects during previous scanning procedures and/or from a modelling of motions of a subject in a scanner.

Advantageously, the method comprises selecting the at least one virtual feature with a feature location at T(0), by providing estimated movements of the subject during a scanning section and selecting the virtual feature with feature location at T(0), to be located such that the virtual feature is subjected to less parameter changes than other virtual features of the subject. In an embodiment, the method comprises selecting the at least one virtual feature with a feature location at T(0), by providing estimated movements of the subject during a scanning section and selecting the virtual feature with feature location at T(0), to be located such that the virtual feature is subjected to less parameter changes than the associated baseline 3D surface representation.

In an embodiment, the surface region comprises a surface region of a body part of the subject, and the virtual feature with a feature location at T(0) is selected to be a virtual feature at least partly located in a central region of the body part at T(0), wherein the central region is defined as a region inside the body part and at a distance to any surfaces of the body part of at least 1 cm, such as at least 2 cm, such as at least 3 cm, such as at least 4 cm, such as at least 5 cm determined from the acquisition arrangement.

In an embodiment, the surface region comprises a surface region of a body part of the subject, and the virtual feature with a feature location at T(0) is selected to be a virtual feature at least partly located in the body portion, which is the target for the scanning.

In an embodiment, the virtual feature with location at T(0) is selected to be a virtual point located at a central region of the head at T(0). In this embodiment, the constraint parameter may for example be a location parameter and/or a distance parameter, such as a parameter of the distance of the virtual point to another virtual feature and/or to an actual feature.

In an embodiment, the virtual feature with a feature location at T(0) is selected to be a virtual line located to cross a central region of the head at T(0). In this embodiment, the constraint parameter may for example be a location parameter, an orientation parameter and/or a distance parameter, such as a parameter of the average distance of the virtual line to another virtual feature and/or to an actual feature.

In an embodiment, the virtual feature with a feature location at T(0) is selected to be a virtual volume located inside and including a central region of the head at T(0), e.g. corresponding to the volume of the head at T(0). In this embodiment, the parameter may for example be a location parameter, distance parameter, an extent parameter, such as a size of the volume and/or an orientation parameter, wherein the volume is not fully rotational symmetrical.

In an embodiment, the virtual feature with a feature location at T(0) is selected to be a virtual area located at a rigid portion of the surface region at T(0). In this embodiment, the parameter may for example be a location parameter, distance parameter, an extent parameter, such as a size of the area and/or an orientation parameter, wherein the area is not fully rotational symmetrical.

In an embodiment, the virtual feature with a feature location at T(0) is selected to be a virtual bone structure also referred to as a rig of bones, preferably comprising at least two virtual bone sections, which may advantageously be interconnected. In this embodiment, the parameter may for example be a location parameter, such as a location parameter of relative location between bone sections of the bone structure; an orientation parameter, such as an orientation parameter of relative orientation of bone sections; a distance parameter, such as a relative location between bone sections of the bone structure and/or any combinations thereof.

The method may preferably comprise dynamically selecting the virtual feature with a feature location at T(0) and the at least one parameter, preferably in dependence of previously detected motions of the subject.

In an embodiment, the at least one constraint comprises a restriction of two or more parameters, which may be of same or different parameter type, such as a parameter type comprising one or more location parameters, a parameter type comprising one or more orientation parameters, a parameter type comprising one or more extent parameters and/or a parameter type comprising one or more distance parameters. The restrictions of the two or more parameters may advantageously be parameters in respective two or more DOF.

In an embodiment, the method comprises determining the best-fit registration of the subsequent 3D surface representation with at least two constraints relative to the baseline 3D surface representation. For example, the method may comprise determining the best-fit registration of the subsequent 3D surface representation with N constraints relative to the baseline 3D surface representation, wherein N advantageously is up to 10, such as 2 to 8, such as 3-6.

Each of the constraints and/or each of the constraint parameters independently of each other may have at least one, preferably 1-6 DOFs. Advantageously, each of the constraints or each of the parameters of the constraints, independently of each other is associated to a set of weight attributes comprising at least one weight attribute, preferably comprising at least 2 weight attributes, such as up to 6 weight attributes, wherein each weight attribute is associated to respective DOF and represents the weight of the constraint of the specific DOF.

The constraint may advantageously have at least one parameter for each DOF of the constraint. The parameter for respective DOFs of the constraint may be equal or may differ from each other.

In an embodiment, the method comprises selecting a plurality of constraints for one or more virtual features and preferably selecting the set of weight attribute for the respective constraints, where the weight of the constraints are selected in dependence of the parameter of the constraint and preferably of the baseline parameter (i.e. the parameter at T(0)).

In an embodiment, the surface region is a surface region of a body part comprising a body portion to be scanned, and wherein the at least one virtual feature comprises a (3D or 2D) cloud of points located inside the body part.

The cloud of points may e.g. comprises points at location determined by a Gaussian function around a central location (rotational center) of the body part, such as a head.

The ROI of the baseline 3D surface representation comprises a set of locations at the surface region, wherein at least a set of points of the cloud points are associated to the ROI of the baseline 3D surface representation. The method may e.g. comprise inserting a plurality of point to form the cloud of point. The cloud of points may individually of each other be associated to the baseline 3D surface representation by being associated to a ROI of the baseline 3D surface representation, where the ROI advantageously may be or comprise a point or a set of points. Thereby the cloud of points association to the baseline 3D surface representation may be individually constrained i.e. forming a cloud of constraint. Each constraint may have one or more weights as described above and the weight(s) of each constraint may be fixed or may be dynamically adjusted.

The center of the cloud would be the location, which is believed to be a rotational center for realistic head motion.

The points are advantageously positioned using a Gaussian distribution around the center to compensate for the fact that no single fixed point location exists, since this depends on the type of head motion.

The density and size of the cloud may be determined by the number of points and the Gaussian standard deviation, respectively.

The density and size of the cloud of points may be dynamically adjusted.

The set of points of the cloud points may advantageously comprise two or more points, such as at least 5 points of the cloud points, such as at least 10, such as at least 15 points of the cloud points, wherein the points of the cloud points may be individually associated to the ROI and/or group wise associated to the ROI, wherein a group-wise association to the ROI, may comprise that a line between two or more points of the cloud points is associated to the ROI. As mentioned above it may be beneficial to illuminate and/or projecting light onto the surface region.

In an embodiment, the method comprises projecting light onto the surface region. The light may be visible (i.e. in the range 380 to 700 nanometers) and/or invisible to human eyes (i.e. outside the range 380 to 700 nanometers.

The projected light or at least a portion thereof is conveniently detectable by the acquisition arrangement.

In an embodiment, the projected light is a simple illumination, e.g. comprising polychromatic light.

In an embodiment, the projected light comprising a structured projected light, preferably the structured light in a cross-sectional plan of its propagation direction has optically distinguishing areas, optionally in form of a pattern.

Examples of optically distinguished areas includes a pattern of areas of light and areas of no-light and/or areas of light of a first quality of a character and areas of light of a second quality of the character, wherein the character advantageously is selected from light intensity, wavelength and/or range of wavelengths.

In an embodiment, the method comprises projecting light onto the surface region, wherein the projected light comprises monochromatic light (same frequency), preferably a coherent light (same frequency and same phase), in this embodiment the reflected light from the surface region may include a 3D pattern, such as a **3*d*** point cloud, a speckle pattern a hologram and/or any combination thereof as well as changes thereof.

In an embodiment, the method comprises projecting light onto the surface region, wherein the projected light comprises a **3*d*** pattern such as a speckle pattern.

The use of speckle techniques for motion sensing may e.g. include using the speckle techniques described in the conference paper by Zizka et al. “SpeckleSense: Fast, Precise, Low-cost and Compact Motion Sensing using Laser Speckle” UIST’11, Oct. 16-19, 2011, Santa Barbara, CA, USA. DOI: 10.1145/2047196.2047261 and/or as described by Relly et al. “Adaptive Noncontact Gesture-Based System for Augmentative Communication” IEEE TRANSACTIONS ON REHABILITATION ENGINEERING, VOL. 7, NO. 2, June 1999.

The method may advantageously be performed using machine learning for selecting virtual feature(s), constraint(s), weight attribute(s), parameter(s) etc.

In an embodiment, the method comprises providing a trained computer system by training a computer system for selecting the at least one virtual feature associated to the baseline 3D surface representation, preferably comprising selecting the ROI of the baseline 3D surface representation, and the at least one constraint using sets of reference data: Each reference data set comprises reference data representing previously determined or modelled movements of a reference subject correlated to reference data representing determined or modelled motions of a reference surface region, wherein the reference surface region is a surface of a reference body part of the reference subject.

In an embodiment the training is a non-supervised training, however it is desirable that the training comprises supervised training, such as partly or fully supervised training.

In an embodiment, the method of training the computer system comprises training the computer system for selecting at least one of number N of constrains (including constraint parameter(s)) and associated virtual features to be applied, respective baline parameter of the virtual features, number X of DOFs of the respective constraint and/or parameter(s) and optionally their respective associated set of weight attributes. The method of training the computer system may comprise training the computer system to dynamically perform the selections.

The reference data representing previously determined or modelled motions of a reference subject advantageously comprises reference data representing motions of the reference body part comprising the reference surface region.

The reference data representing previously determined or modelled motions of a reference subject may comprise reference data representing changes of a parameter of least one reference virtual feature associated to the reference surface region caused by the motions. Preferably, the reference virtual feature is located at the reference surface region or with a distance to the reference surface, such as within a volume of the reference body part.

Advantageously, the reference data representing previously determined or modelled motions of a reference subject comprises reference data representing motions and/or changes of a plurality reference virtual features located inside the reference subject, preferably at least N reference virtual features, wherein N is an integer selected from 1-10, such as up to 8, such as up to 6, such as 2, 3, or 4.

The invention also comprises a motion tracking apparatus for motion tracking of a subject located in a scanner bore preferably using the method as described herein and as claimed in the claims.

The motion tracking apparatus comprises an acquisition arrangement configured for acquiring a 3D surface representation of a surface region of the subject; and a computer system in data communication with the acquisition arrangement for receiving data representing the 3D surface representation, wherein the computer system is configured for i. receiving data representing a 3D surface representation acquired by the camera arrangement at a first point of time and generating a baseline 3D surface representation of the surface region of the subject;

ii. associating at least a portion of the baseline 3D surface representation to at least one virtual feature located at a baseline location;

iii. receiving data representing a 3D surface representation acquired by the acquisition arrangement at a subsequent time and generating a subsequent 3D surface representation of the surface region of the subject and iv. determining at least one motion tracking parameter comprising determining a best-fit registration of the subsequent 3D surface representation with a constraint relative to the baseline 3D surface representation.

The acquisition arrangement is configured for acquiring the 3D surface representation of a surface region of the subject in the form of data representing the 3D surface representation. The acquires the data representing the 3D surface representation by acquiring optical signals e.g. reflected light from the surface region of the subject e.g. in the form of images. The optical signals are conveniently converted to digital signals, e.g. a digital point cloud or a digital 3D image.

In an embodiment, the computer system is configured for controlling a projector arrangement for projecting light onto a surface region of the subject and/or for controlling the acquisition arrangement for acquiring 3D surface representations of the surface region at selected points of time, preferably with a frequency of at least 1 Hz, such as at least 5 Hz, such as 10-500 Hz, such as 20-100 Hz.

The projector arrangement may comprise a projector as described above. The acquisition arrangement may be as described above.

The computer system may be configured for receiving user instructions and/or acquiring instruction from a database, such as instructions relating to at least one of a criterion associated to the scanning procedure to be run by the scanner, a criterion associated to the subject and/or a criterion associated to a location and/or a body part to be scanned.

A criterion associated to the scanning procedure may for example include type of scanning, scanner specifications, scan session protocol, required scanning quality and/or resolution, acquisition method acquisition method settings image acquisition time.

A criterion associated to the subject may for example include gender, age, weight, body fat level and/or medical/psychological condition(s).

A criterion associated to the location and/or body part to be scanned may for example include body part and/or body portion of the subject to be scanned.

The computer system may advantageously be configured for receiving user instructions and/or acquiring instruction from a database relating to at least one of number N of constrains and associated virtual feature(s) to be applied, respective baseline parameter(s) of the respectively virtual features, number X of DOFs of the respective constraint and optionally their respective associated set of weight attributes. Such selection may be provided as generated above e.g. by modeling and/or from previously conducted motion tracking's.

In an embodiment, the computer system is configured for selecting at least one of number N of constrains and associated virtual features to be applied, respective baseline parameter(s) of the respectively virtual features, number X of DOFs of the respective constraint and optionally their respective associated set of weight attributes.

The selection may preferably be performed in dependence on instructions relating to at least one of a criterion associated to the scanning procedure to be run by the scanner, a criterion associated to the subject and/or a criterion associated to a location and/or body part to be scanned. Thus for some motion tracking procedures one single virtual feature and one constraint may be sufficient, whereas for other tracking procedures several virtual features and/or constraints may be desired e.g. as described elsewhere herein.

In an embodiment, the computer system is configured for dynamically selecting at least one of number N of constrains and associated virtual features, to be applied, respective baseline parameter(s) of the respectively virtual features, number X of DOFs of the respective constraint and optionally their respective associated set of weight attributes.

In an embodiment, the computer system is a programmed computer system, comprising a one or more computers programmed to perform the steps i-iv and preferably, to carry out the method as described above.

The computer system may beneficially comprise a trained computer, wherein the trained computer has been trained for selecting at least one of number N of constrains and associated virtual features, to be applied, respective baseline parameter(s) of the respectively virtual features, number X of DOFs of the respective constraint and optionally their respective associated set of weight attributes.

The trained computer may advantageously be trained for dynamically selecting at least one of number N of constrains and associated virtual features, to be applied, respective baseline parameter(s) of the respectively virtual features, number X of DOFs of the respective constraint and optionally their respective associated set of weight attributes.

The trained computer may in an embodiment, be an AI computer e.g. trained by non-supervised training.

In an embodiment, the trained computer is a computer subjected to machine learning, preferably been trained by a method as described above. The trained computer may for example comprise a neural network.

The trained computer may advantageously be trained to receive receiving user instructions via an interface, wherein the user instructions comprises to at least one of a criterion associated to the scanning procedure to be run by the scanner, a criterion associated to the subject and/or a criterion associated to a location and/or body part to be scanned.

The training of the trained computer may advantageously include training the computer to select at least one of at least one constraint, number of DOF of the at least one constraint, weight attribute(s) and/or parameter(s) of the constraint, at least one virtual feature, location and/or orientation thereof. The computer may be trained to perform the selection(s) and/or determination(s) as described above.

The computer may be trained to perform the selection of at least one of at least one constraint, number of DOF of the at least one constraint, weight attribute(s) and/or parameter(s) of the constraint, at least one virtual feature, location and/or orientation thereof at least partly based on modelling of expected movements of an anatomical model of at least one body part of the subject comprising the surface region of the subject and correlating the movements of the anatomical model to movements of the surface region, movements of potential virtual features and movements of the body portion which is target for the scanning. The potential virtual features may comprise preselected potential virtual features. In an embodiment, movements of the anatomical model is supplemented or replaced by data of movements of subjects observed in previous scanning procedures.

Further details of methods of training the computer/computer system are provided in the description of the figures and examples and elements thereof.

All features of the inventions and embodiments of the invention as described herein including ranges and preferred ranges may be combined in various ways within the scope of the invention, unless there are specific reasons not to combine such features.

DESCRIPTION OF CERTAIN EMBODIMENT, EXAMPLES AND ELEMENT ILLUSTRATING THE INVENTION

Brief description of preferred embodiments and elements of the invention.

The above and/or additional objects, features and advantages of the present invention will be further elucidated by the following illustrative and non-limiting description of embodiments, examples and elements of the present invention, with reference to the appended drawings.

The figures are schematic, are not drawn to scale, and may be simplified for clarity. Throughout, the same reference numerals are used for identical or corresponding parts.

FIG. 1 schematically illustrates an embodiment of a motion tracking apparatus arranged for tracking of a subject located in a scanner bore.

FIG. 2 schematically illustrates a scanning bore of a scanner seen in an end view.

FIG. 3 schematically illustrates a variation of scanning bore of a scanner of FIG. 2 seen in a side view.

FIGS. 4*a* and 4*b* illustrates a tracking session of a head of an embodiment of the method according to the invention.

FIG. 4*c* illustrates a tracking session of a head of another embodiment of the method according to the invention.

FIGS. 5*a*-5*c* illustrates different potentially determined head motions.

FIGS. 6*a* and 6*b* illustrate respective tracking sessions of a knee region applying different virtual features and constraints.

FIGS. 7*a*-7*c* illustrate a tracking session of a body part with and without constraint.

FIGS. 8*a*-8*c* illustrate a tracking session of a body part with and without constraints, wherein a plurality of virtual features are applied.

Figure 1:
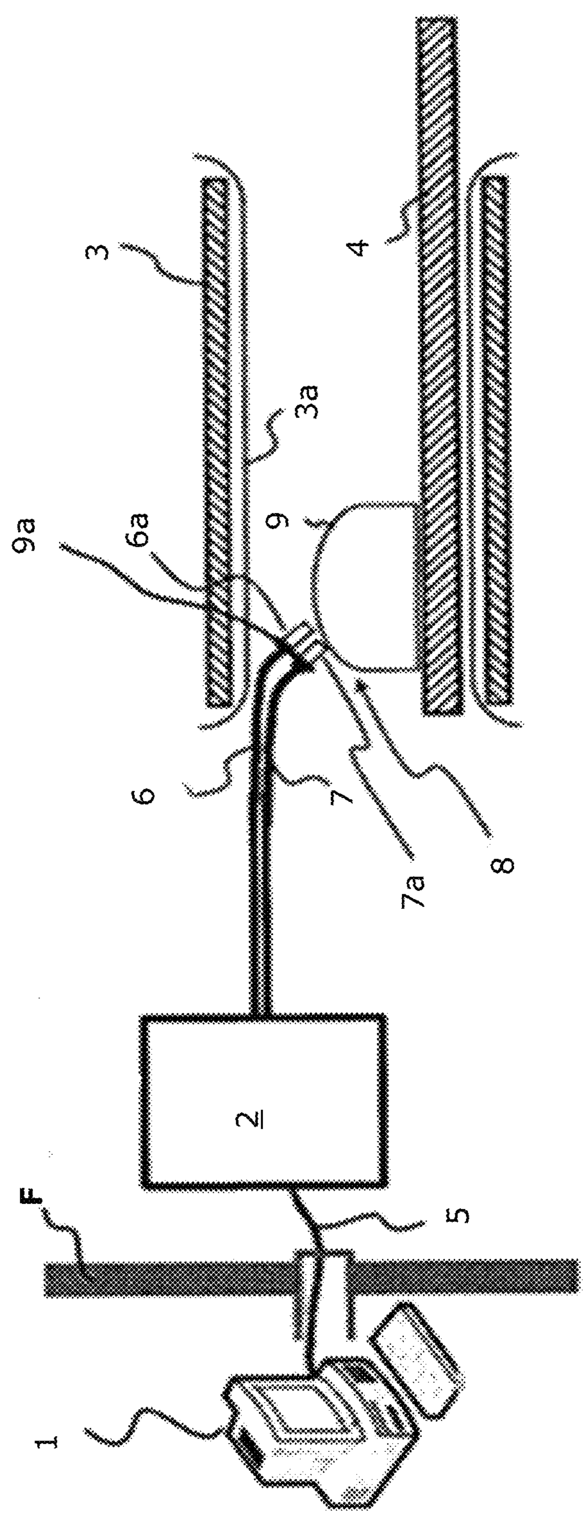
Figure 2:
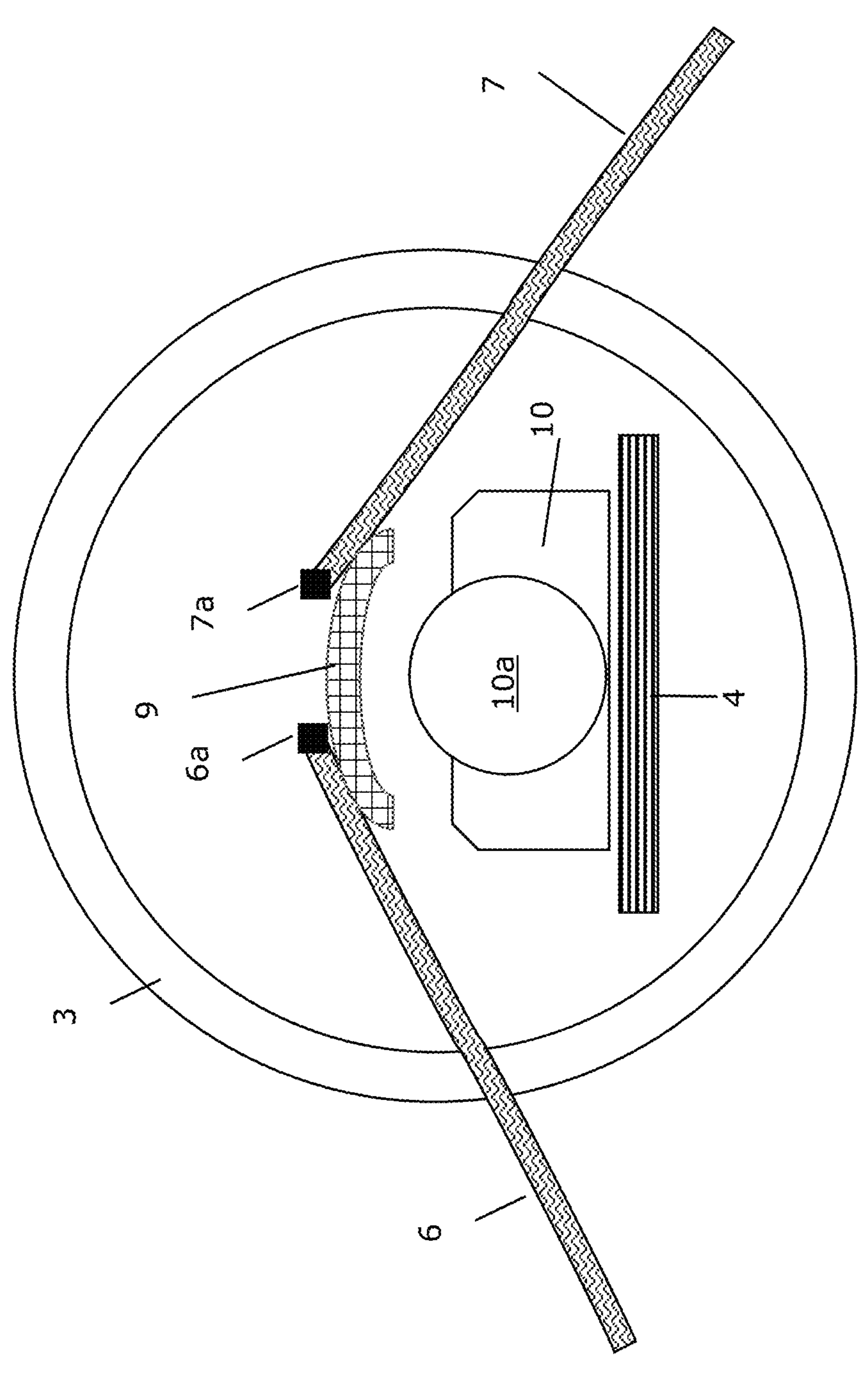

The motion tracking apparatus shown in FIG. 1 comprises a controller 2 a computer 1 a first bundle of optical fibers 6 with a first lens assembly 6*a,* a second bundle of optical fibers 7 with a second lens assembly 7*a.*

The controller may include a not shown control computer. The computer system of the motion tracking apparatus may thus comprise the control computer, the computer 1 as well as further computing units or digital memories configured for being in data communication with the control computer and/or the computer 1. The motion tracking apparatus comprises a projector arrangement for projecting light onto the surface region of the not shown subject. The projector may comprise a light source e.g. included in the controller 2 and the first bundle of optical fibers 6 with the first lens assembly 6*a* arranged for projecting light onto the surface region. A frame 9*a* may be applied fixing the position between the first and second lens assemblies 6*a,* 7*a* and/or between the distal ends of the first and second optical fibers 6, 7 respectively and optionally for fixing to the head coil 9.

The motion tracking apparatus comprises an acquisition arrangement configured for acquiring a 3D surface representation of a surface region of the subject i.e. in the form of data representing the 3D surface representation as described above. The acquisition arrangement comprises the second bundle of optical fibers 7 with a second lens assembly 7*a*. The optical signals are collected via the second lens assembly 7*a,* relayed via the bundle of optical fibers 7 to an optical sensor arrangement e.g. a camera located in the controller 2.

The scanner bore 8 may be a scanner bore of any type of scanner. In an embodiment, the scanner bore 8 is a MR scanner bore and the scanner comprises a permanent magnet 3 in a scanner housing 3*a* forming the scanner bore 8. The scanner comprises a head coil 9 for scanning a not shown subject positioned on the support structure (bearing) 4.

In the shown embodiment, a shielding wall F is located to form a Faraday cage protecting the computer 1 from the magnetic field inside the scanner bore 8. A data line e.g. an optical extender 5 is arranged for transfer data substantially noiseless (preferably noise less than 50 dB or even less than 30 dB in the range 20 Hz to 20 kHz) between the controller 2 and the computer 1 outside the scanner bore.

In the shown embodiment, the controller is located inside the scanner room defined by surrounding walls F illustrated here by a wall 52 to the left side controller 2. The controller 2 may then conveniently be surrounded by a not shown shielding housing, which functions as a radio frequency shielded box. The housing may be made out of a frame, e.g. a wooden frame, covered by a 1 mm copper layer. A filter of capacitors may be arranged to ensure that electromagnetic noise from powering the components inside the housing does not propagate along the power cable. The power supply optionally being a separate not shown power supply.

In a variation thereof, the controller 2 may be located outside the scanner room defined by surrounding walls F if the optical fibers 16, 20 are sufficiently long.

In a further variation, the scanner is a PET scanner or a combined MR/PET scanner.

Figure 3:
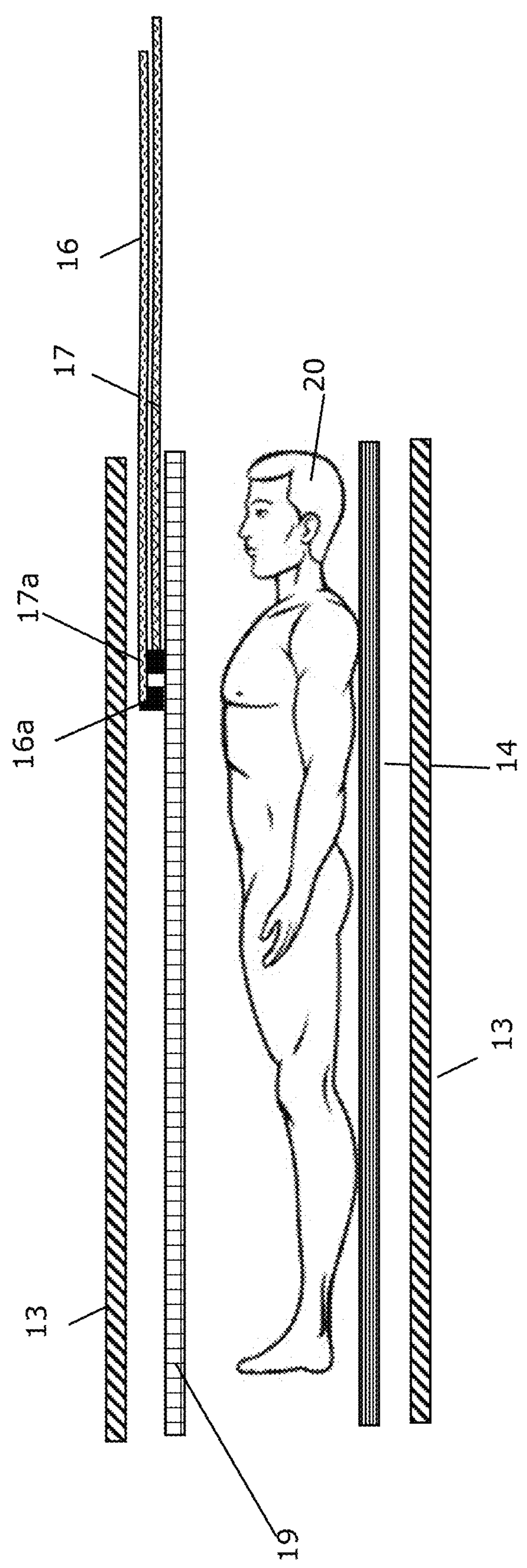

The scanner bore shown in FIG. 3 corresponds to the scanner bore of FIG. 1. In this embodiment only a part of the tracking apparatus is shown, namely the first bundle of optical fibers 6 with the first lens assembly 6*a* arranged for projecting light onto the surface region and the second bundle of optical fibers 7 with a second lens assembly 7*a* for acquisition of light signals reflected from the surface region of the subject.

In this embodiment the first and second lens assemblies 6*a,* 7*a* are located with a distance to each other for providing an angle against the projected light and the acquired light signals The distal end of respectively the first bundle of optical fibers 6 and the second bundle of optical fibers 7, are fixed to the head coil 9.

A subject 10, e.g. a patient is lying on the bearing 4, with the body part, here the head 10*a,* located below the head coil 9.

The scanning bore of a scanner of FIG. 3 seen in a side view, with a part of the scanner coil cut out to see the subject 20, located on the bearing 14.

A coil 19 is located for acting as an antenna to receive the radio frequency signal from the relevant body portion during scanning. A first bundle of optical fibers 16 with the first lens assembly 16*a* arranged for projecting light onto the surface region is removable or adjustable fixed to the coil 19 at a desired location. In the same way a second bundle of optical fibers 7 with a second lens assembly 7*a* for acquisition of light signals reflected from the surface region of the subject are removable or adjustable fixed to the coil 19 at a desired location. By changing location of the first lens assembly 16*a* and/or the second lens assembly, the surface region to be subjected to the motion tracking may in a simple way be changed or adjusted, e.g. in dependence of the body portion to be subjected to the scan and/or the surface region of the subject, e.g. the surface region of the body part comprising the body portion to be subjected to the scan.

Figures 4A, 4B:
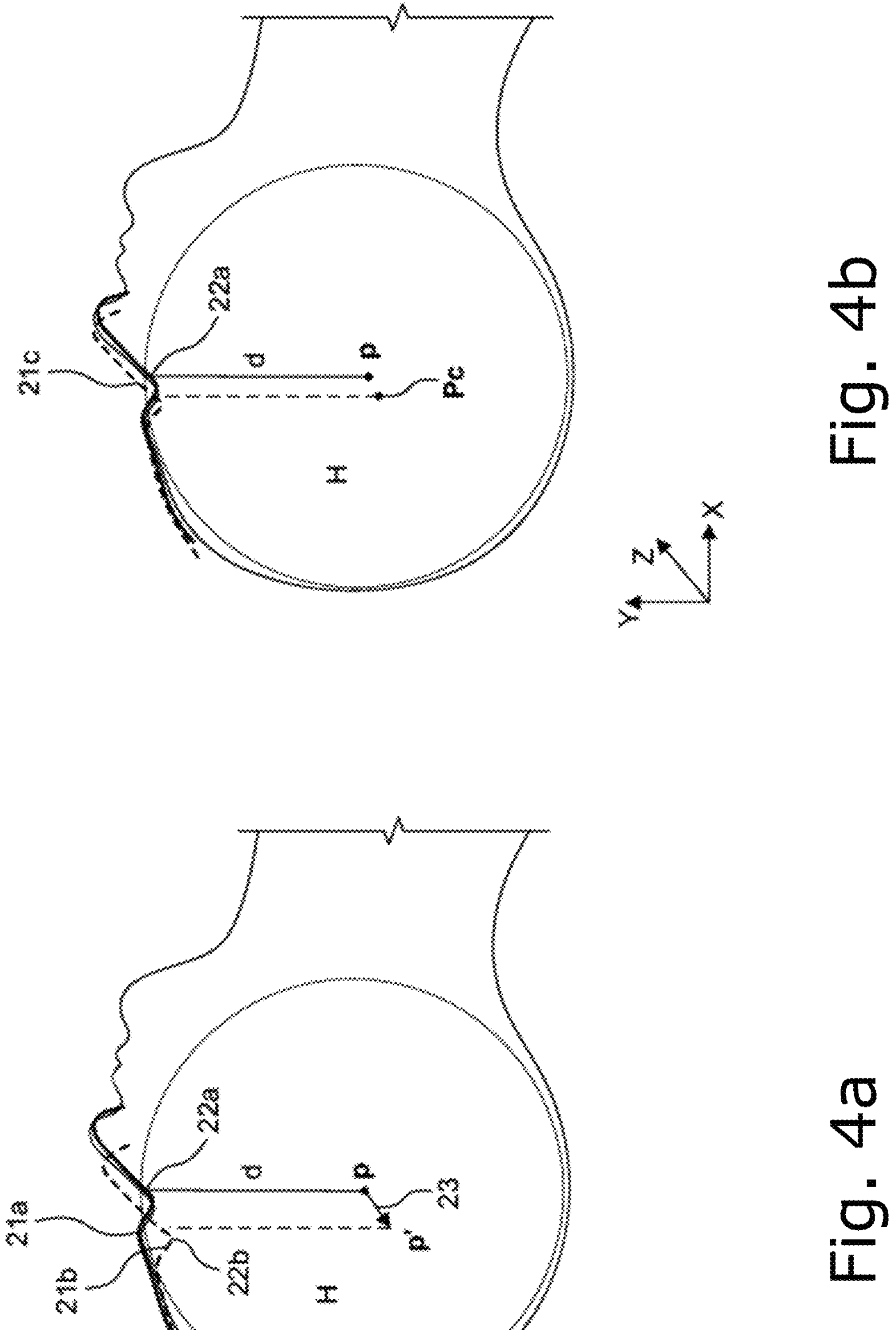
Figure 4C:
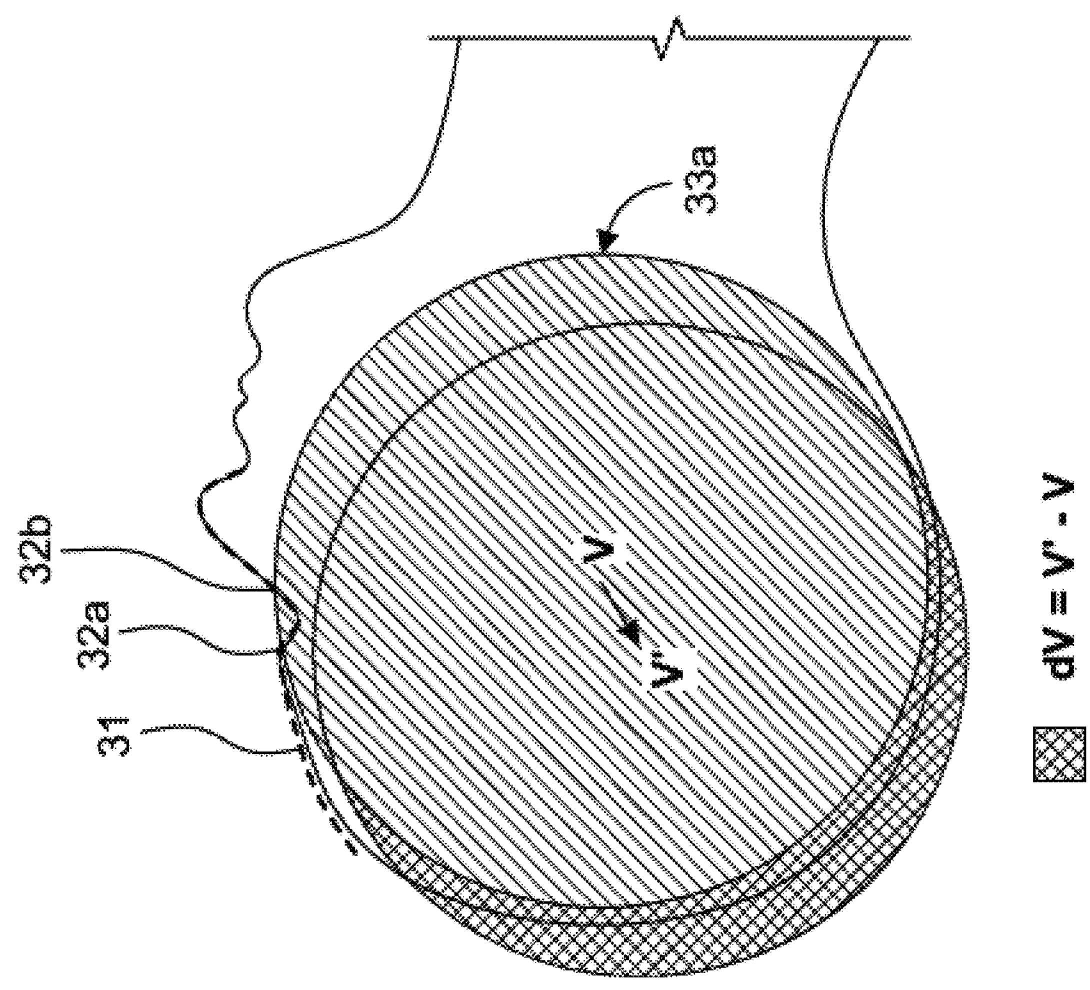

FIG. 4*a* illustrates a tracking session wherein the body part is a head H of a subject and the body portion subjected to scanning may be the brain. The head H is illustrated in a cross-sectional side view.

In this example of the method, a baseline 3D surface representation is determined by generating a baseline 3D surface representation 21*a* of a surface region of the subject at a first point of time (T(0)). The surface region comprises a nasal bridge of the subject. A virtual point P is selected by the computer or by an operator to be located in the center of the head. The virtual point P is associated to the baseline 3D surface representation 21*a*. In this example, the virtual point P is associated to a ROI in the form of a selected location 22*a* of the baseline 3D surface representation 21*a*. The location 22*a* is selected to provide a vertical distance lined to the virtual point P. The distance lined has a length and an orientation, which in this embodiment is vertical. In variations thereof the distance line may be non-vertical, e.g. with a selected angle to vertical and/or the virtual point P be associated to an ROI of the baseline 3D surface representation 21*a* comprising a plurality locations of the baseline 3D surface representation 21*a,* each location having an orientation and a distance to the virtual point P.

As illustrated in FIG. 4*a*, the vertical orientation is an orientation along a y direction of a 3D coordinate system with the axis X, Y and Z. In a variation of the illustrated embodiment as described above, the virtual point P is associated to an ROI in the form of a selected location 22*a* of the baseline 3D surface representation 21*a,* wherein the location 22*a* is selected to provide a distance lined along the Y axis to the virtual point P, a not shown distance along the X axis to the virtual point P and a not shown distance along the Z axis to the virtual point P.

At a subsequent point of time (T(s)), the method comprises generating a subsequent 3D surface representation of the surface region 21*b*. By the association between the virtual point P and the location 22*a* of the baseline 3D surface representation 21*a,* the corresponding virtual point P' associated to a corresponding ROI in the form og the corresponding location 22*b* of the subsequent 3D surface representation 21*b* can be determined. It can be seen that the virtual point P' of the subsequent 3D surface representation 21*b* has been shifted relative to the virtual point P of the baseline 3D surface representation by a shift 23 which may be described as relative distances along the X, Y and Z axis. Here only the shifts along the Y and X axis' are shown. One or more constraints are in accordance with the method applied to suppress false motions and/or detection errors to thereby obtain a more accurate best-fit registration of the subsequent 3D surface representation 21*b* to determine a more accurate motion of the head H.

In this embodiment the constraint may conveniently comprise a restriction of shifts of the virtual point P to the subsequent virtual point P' along one or more of the X, Y and Z axis' (1-3 3DOF). The selected constraint may be selected as described above, preferably based on a knowledge of atomically plausible and anatomically implausible motions of the body part in question, here the head H. This knowledge may be generated by a modeling procedure, by observing subjects motions and/or by previous tracking procedure(s). In this embodiment, the constraint may conveniently comprise a restriction of the shift 23 along the X direction, since motions along the X direction of the head H generally may be restricted. Thus the restriction of the shift 23 along the X axis would conveniently be selected to be a rather high constraint, such as a restriction of 50% or higher, such as a restriction of 75-90%. In addition, the restriction of the shift 23 along the Y axis would conveniently be selected to be a function of the restriction of the shift 23 along the Y axis "y" for example the restriction may provide that only where y exceeds a selected threshold T(Y) the shift along the Y direction is restricted and where only the part of y exceeding the threshold is restricted with a selected percentage (PRC), i.e. the restricted shift R(Y) along the Y axis (i.e. after applying the restriction) may be as follows: Where y<T(y)=no restriction; where y>T(Y), R(Y)=T(Y)+PRC*(y−T(Y).

The virtual point Pc associated to the corresponding ROI of the best-fit representation of the surface region 21*c* is illustrated in FIG. 4*b*.

In this example of the method, a baseline 3D surface representation is determined by generating a baseline 3D surface representation 31 of a surface region of the subject at a first point of time (T(0)). The surface region comprises a nasal bridge of the subject. A virtual feature is selected to be a volume virtual feature, namely a volume V inscribed in a circle 33*a* and having a center corresponding to the center of the head H.

The virtual volume V is associated to the baseline 3D surface representation 31, by the circle 33*a* crossing the baseline 3D surface representation 31 of the surface region at the ROI in the form of two locations 32*a,* 32*b*.

At a subsequent point of time (T(s)), the method comprises generating a not shown subsequent 3D surface representation of the surface region. By the association between the virtual volume V and the locations of the circle 33*a* crossing the baseline 3D surface representation 31, the location of the volume V' and the circle 32*b* inscribing the volume V' associated to the corresponding ROI of the subsequent 3D surface representation of the surface region may be determined. It can be seen that the virtual volume V' has been shifted relative to the virtual V by the shift dV=V'−V. It can be seen that the shift comprises a displacement along at least the Y axis and the X axis.

One or more constraints are in accordance with the method applied to suppress false motions and/or detection errors to thereby obtain a more accurate best-fit registration of the subsequent 3D surface representation to determine a more accurate motion of the head H.

The constraint may advantageously comprise a 3 DOF, such as a constraint with respective weights of shifts along respective axis (X, Y, Z).

Figures 5A, 5B, 5C:
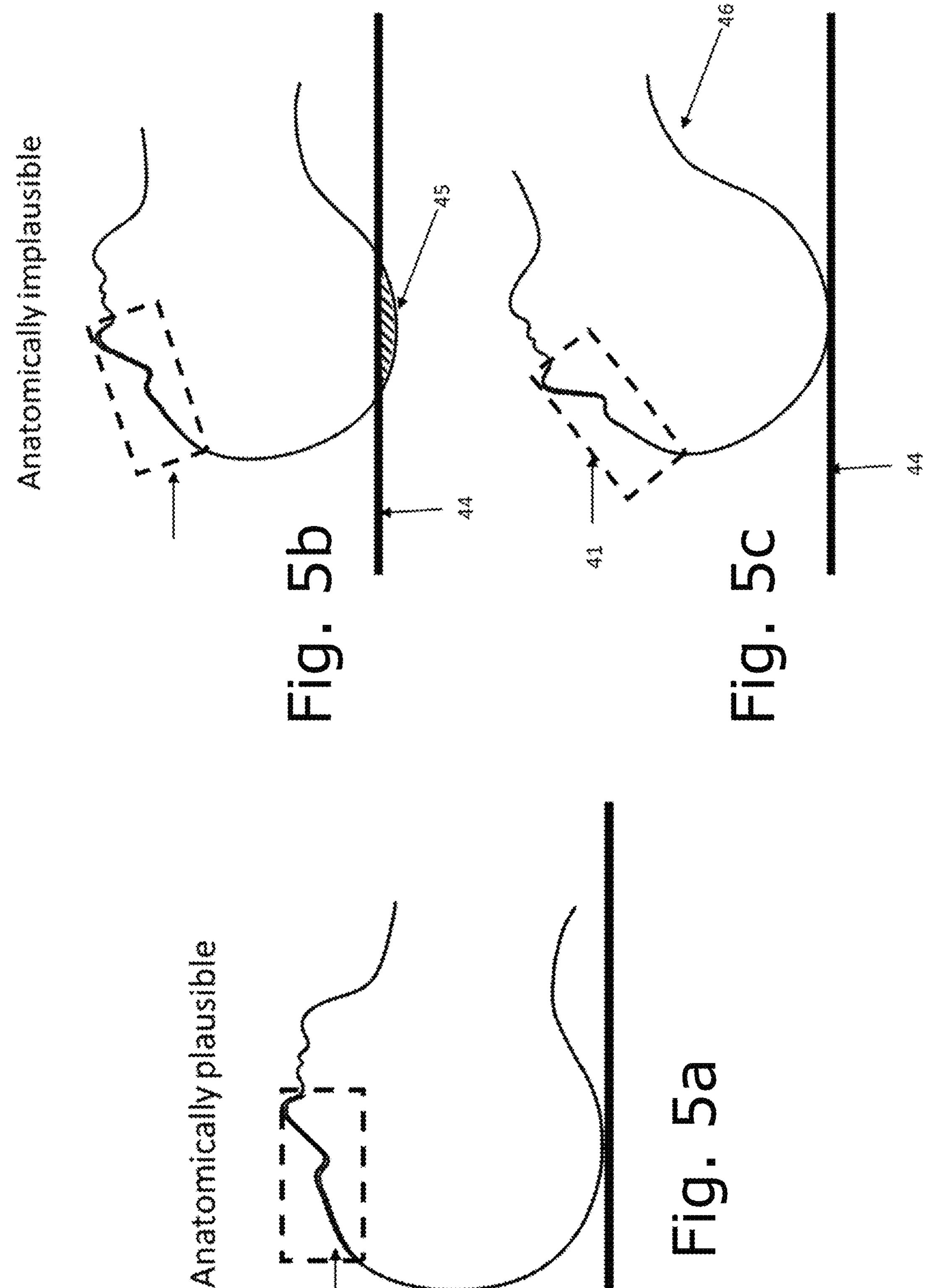

FIGS. 5*a*-5*c* illustrates different potentially determined head motions.

In FIG. 5*a*, the subject is resting the head H on the bearing 44 in a highly anatomically plausible position, thus any subsequent 3D surface representation of the surface region, which indicate motion(s) to such a position may be deemed plausible and no constraint may be required. The reference no. 41 indicates the surface region, which may conveniently be tracked for generating baseline 3D surface representation and subsequent 3D surface representations of the surface region.

FIG. 5*b* illustrates an anatomically implausible position of a subjects head H. Specifically it should be noted that the bac region 45 of the head goes below the bearing 44. This would only be possible where the bearing is high compressible or elastic. Usually only a minor depressing into the bearing may be plausible. Any motions to such a position as illustrated in FIG. 5*b* may be deemed implausible and a subsequent 3D surface representation of the surface region indicating motions involving such position may comprise false motion and/or detection errors. By applying one or more constraints as described above such comprise false motion and/or detection errors may be suppressed.

FIG. 5*c* illustrates another anatomically implausible position of a subjects head H. Specifically it should be noted that the neck region 46 of the head is angled in an orientation, which for most subjects would not be possible when lying in a canner bore. Smaller motions of the neck region may be more plausible, depending on the space where the head is located during the scan. Any motions to such a position as illustrated in FIG. 5*c* may be deemed implausible and a subsequent 3D surface representation of the surface region indicating motions involving such position may comprise false motion and/or detection errors. By applying one or more constraints as described above such comprise false motion and/or detection errors may be suppressed.

Figures 6A, 6B:
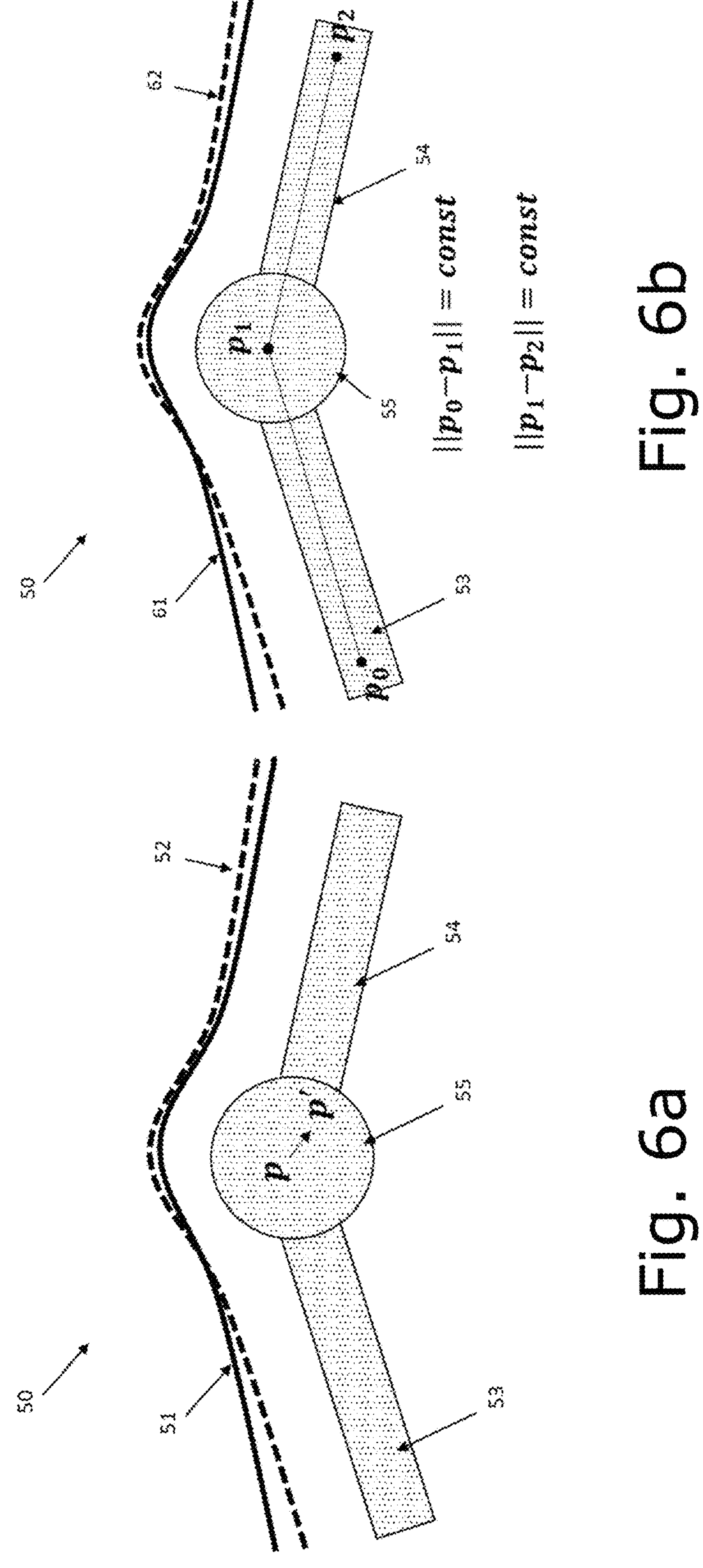

FIG. 6*a* illustrates a tracking session wherein the body part is a knee region 50 of a subject and the body portion subjected to scanning may be the internal soft-tissue structures of the knee joint. For increasing the accuracy, the surface region tracked comprises a surface portion of the knee joint as well as a surface portion of the femur and a surface portion of the tibia. As seen in the illustration, the joint region 55 is illustrated as a circular volume and the femur bone 54 and the tibia bone are extending from the joint region 55.

In this example of the method, a baseline 3D surface representation is determined by generating a baseline 3D surface representation 51 of a surface region of the knee region at a first point of time (T(0)). A virtual point P is selected by the computer or by an operator to be located in the center of the circle representing the knee joint 55. The virtual point P is associated to a ROI of the baseline 3D surface representation 51. The ROI advantageously comprises at least a point at the surface portion of the knee joint, a point at the surface portion of the femur and a point of the surface portion of the tibia. The virtual point P may be associated to the ROI of the baseline 3D surface representation by the methods as described above.

At a subsequent point of time (T(s)), the method comprises generating a subsequent 3D surface representation 52 of the surface region. By the association between the virtual point P and the ROI of the baseline 3D surface representation 51, the location of the corresponding virtual point P' associated in a corresponding way to the corresponding ROI of the subsequent 3D surface representation of the surface region may be determined.

It can be seen that the virtual point P' of the subsequent 3D surface representation 52 has been shifted relative to the virtual point P of the baseline 3D surface representation. One or more constraints are in accordance with the method applied to suppress false motions and/or detection errors to thereby obtain a more accurate best-fit registration of the subsequent 3D surface representation 21*b* to determine a more accurate motion of the head H.

FIG. 6*b* illustrates another tracking session wherein the body part is a knee region 50 of a subject as in example 6*a*.

The body portion subjected to scanning may be the internal soft-tissue structures of the knee joint. For increasing the accuracy, the surface region tracked comprises a surface portion of the knee joint as well as a surface region of the femur and a surface region of the tibia. As seen in the illustration, the joint region 55 is illustrated as a circular volume and the femur bone 54 and the tibia bone are extending from the joint region 55. In this example of the method, a baseline 3D surface representation is determined by generating a baseline 3D surface representation 61 of a surface region of the knee region at a first point of time (T(0)). At least three virtual points P0, P1, P2 are selected by the computer system or by an operator to be located respectively in a center location (P1) of the circle inscribing the knee joint 55 and in respectively a center location (P2) of the femur bone and a center location (P0) of the tibia bone.

The respective virtual points P0, P1, P2 may be associated to a ROI of the baseline 3D surface representation, wherein the ROI advantageously comprises at least a point, ROI-1 at the surface portion of the knee joint, a point ROI-1 of the surface portion of the femur and a point ROI-0 of the surface portion of the tibia, where P0 is associated to ROI-0, P1 is associated to ROI-1 and P2 is associated to ROI-2.

At a subsequent point of time (T(s)), the method comprises generating a subsequent 3D surface representation 62 of the surface region. By the association between the respective virtual points P0, P1, P2 and the baseline 3D surface representation 61, the location of the corresponding respective virtual points (not shown) associated in a corresponding way to the corresponding ROI comprising the corresponding points ROI-0, ROI-1 and ROI-2 of the subsequent 3D surface representation of the surface region. One or more constraints may be applied to suppress false motions and/or detection errors to thereby obtain a more accurate best-fit registration of the subsequent 3D surface representation 52 to determine a more accurate motion of the head knee region. The restraints applied may advantageously, comprise keeping the respective distances P0 to P1 and P1 to P2 constant or restriction changes of the distance to a minimum.

Figures 7A, 7B, 7C:
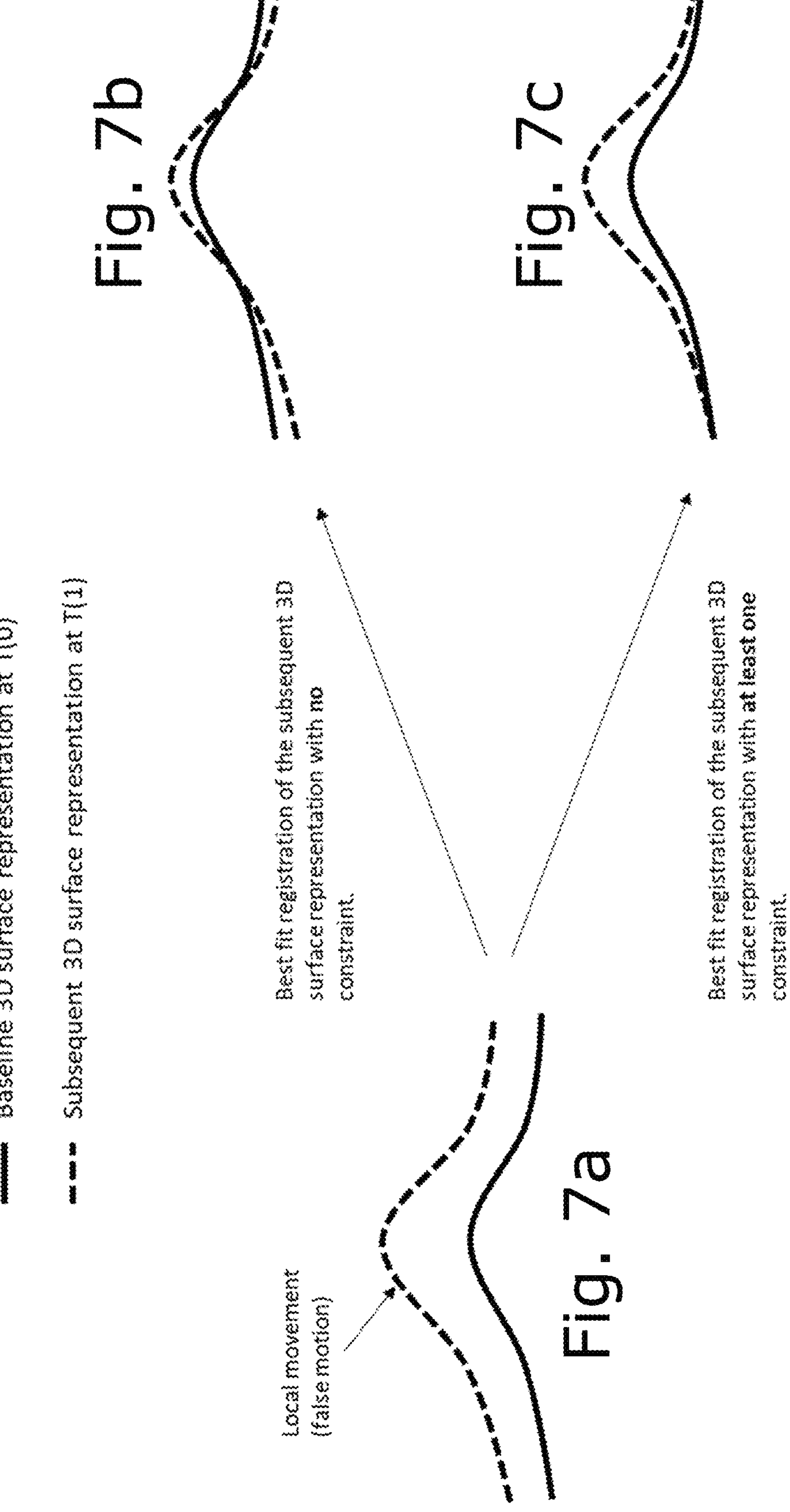

FIGS. 7*a*-7*c* illustrates a tracking session of a body part with and without constraint.

FIG. 7*a* illustrates a baseline 3D surface representation of a surface region generated at T(0) and a subsequent 3D surface representation of the surface region generated at T(1) before the best fitting step. The subsequent 3D surface representation includes data of a local movement, such as a movement that does not correspond to any movements of the body portion, which is subject for the scanning, such as a movement of soft tissue.

In FIG. 7*b*, a best-fit registration of the subsequent 3D surface representation of the surface region without any constraints is illustrated. This tracking result includes the tracking of the false motion without any suppression thereof and therefor this tracking result may result in that a scanning parameter may be adjusted unnecessarily (and e. case the scanning to be of low quality or even useless) and/or it may result in that the scanning is stopped and/or restarted unnecessarily.

In FIG. 7*c*, a best-fit registration of the subsequent 3D surface representation of the surface region with at least one constraint is illustrated. In this tracking result, the false motion has been suppressed which ensures a tracking quality of a highly improved quality.

FIGS. 8*a*-8*c* illustrates a tracking session of a body part with and without constraint, wherein the body part comprises a bone structure B and where the bone structure B below a skin area and where the bone structure B contributing to shaping the surface region of the subject in the scanner. The bone structure may e.g. comprise a joint region or a region of a face.

FIG. 8*a* illustrates a baseline 3D surface representation of the surface region generated at T(0) and a subsequent 3D surface representation of the surface region generated at T(1) before the best fitting step. The subsequent 3D surface representation includes data of a local movement, such as a movement that does not correspond to any movements of the body portion, which is subject for the scanning, such as a movement of soft tissue. The movement may e.g. be a movement caused by face muscles, where there may be none or only minor movement of the bone structure B.

The bone structure B may be known or estimated from a bone structure model and/or from one or more previous or simultaneously acquired image(s), such as ultrasound image(s), X-ray image(s), and/or MR image(s).

The method comprises in this embodiment selecting a plurality of virtual features in the form of virtual points P located at the bone structure surface area and associating each of the virtual features to a location of the baseline 3D surface representation at respective location corresponding to the shortest distance between virtual feature P and location of the baseline 3D surface representation. The distance between each of the respective virtual points their respective associated points (ROI) of a ROIs of the baseline 3D surface representation is referred to as a distance line and these distance lines are here illustrated as extension/compression springs D1, D2, D3.

In FIG. 8*b*, a best-fit registration of the subsequent 3D surface representation of the surface region without any constraints is illustrated. The virtual points p are associated to respective corresponding points (cROI) if the corresponding ROI of the subsequent 3D surface representation of the surface region. The best-fit registration without any constraint is here a "rigid" registration. Here the distance lines d1, d2, d3 without restrictions are illustrated. This tracking result includes the tracking of the false motion without any suppression thereof and therefor this tracking result may result in that a scanning parameter may be adjusted unnecessarily because the internal body portion, which is the target for the scanning has not moved or only slightly moved, whereas the surface region may have been subjected to much larger movements. The resulting scanning may then be of low quality or even useless and/or it may result in that the scanning is stopped and/or restarted unnecessarily.

In FIG. 8*c*, a best (non-rigid) fit registration of the subsequent 3D surface representation of the surface region with at least one constraint comprising a restriction of the length of each of the distance lines (also called extension/compression springs) D1, D2, D3 is illustrated. In this tracking result, the false motion has been suppressed which ensures a tracking of a highly improved quality.

The restriction of the respective length of the distance lines (extension/compression of springs) D1, D2, D3 may advantageously be such that at least two of the restrictions differs from each other.

The distance lines are here considered as the extension/compression springs D1, D2, D3, which has outset lengths (L(0)) determined in respect of the baseline 3D surface representation and wherein the change of spring length of each of the respective is restricted by a value k, which may be a constant or it may be a function. For example the extension/compression springs D1, D2, D3 may be restricted by the respective values k1, k2, k3, wherein at least one of the values k1, k2, k3 may differ from at least one other of the values k1, k2, k3.

In an embodiment, one or more of the values k1, k2, k3 the k value is/are a function, which is/are dependent of dependent of another distance line (d1, d2 or d3) in respect of the subsequent 3D surface representation of the surface region without constraint. For example, each of the k values k1 and k3 for respectively the extension/compression spring D1 and the extension/compression spring D3 may be depended on the unrestricted distance line d3 and/or the value k2 for the extension/compression spring D2 may be dependent on one or both of the distance lines d1 and d3.

Figure 9:
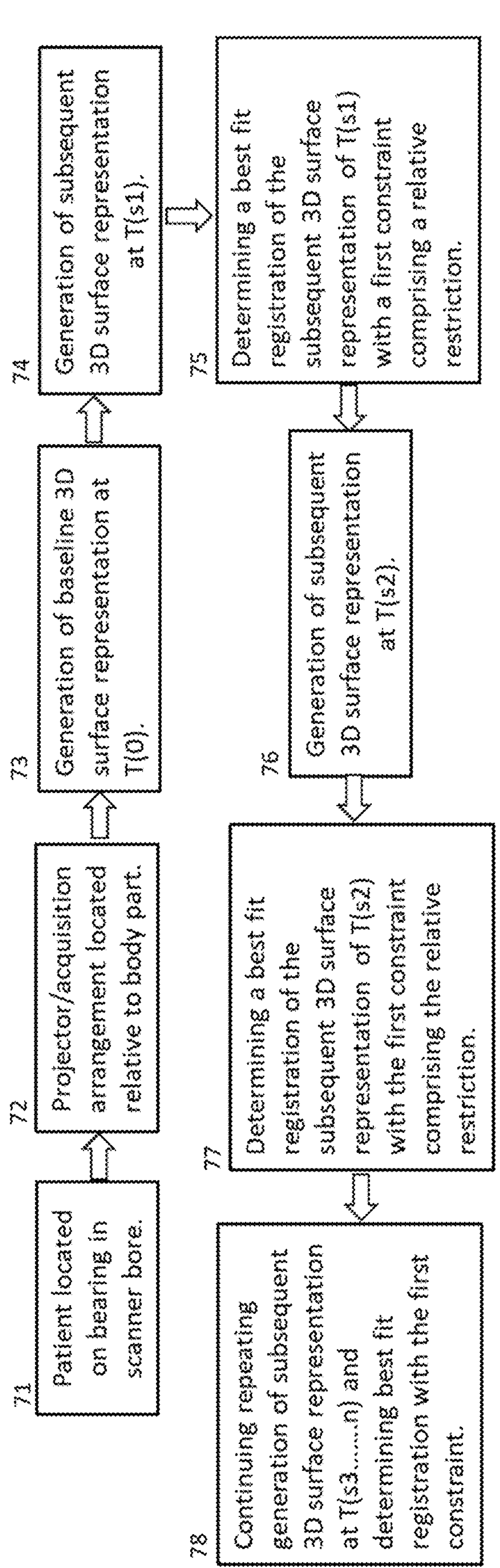
FIG. 9 is a process diagram of an embodiment of the method according to the invention.

The process diagram shown in FIG. 9, illustrated of an embodiment of the method according to the invention wherein a body portion is subjected to a scanning procedure and a surface region of a body part comprising the body portion is performed.

In step 71, the patient (a subject) is located on and supported by a bearing. The bearing is located in a bore of a scanner e.g. a MR scanner, a CT scanner or any other scanner as described above. Step 72 illustrated that an acquisition arrangement for acquiring reflected light data for generating 3D surface representations of the surface region is or has been arranged in a desired location and orientation relative to the surface region of the body part. In addition, a projector arrangement for imaging the surface region or optionally projecting structured light (e.g. a light pattern) onto the surface region may be or has been arranged in a desired location and orientation relative to the surface region of the body part. The steps 71 and 72 may be in any order.

In step 73, the tracking apparatus generates a baseline 3D surface representation at T(0).

In step 74, the tracking apparatus generates a subsequent 3D surface representation at T(s1).

In step 75, the tracking apparatus determines a best-fit registration of the subsequent 3D surface representation of T(s1) with at least one first constraint comprising a relative restriction.

In step 76, the tracking apparatus generates a further subsequent 3D surface representation at T(s2).

In step 77, the tracking apparatus determines a best-fit registration of the subsequent 3D surface representation of T(s2) with the at least one first constraint comprising the relative restriction.

Step 78 illustrates that the tracking apparatus continues repeating generation of subsequent 3D surface representation at T(s3 . . . n) and determining best-fit registration at least with the first constraint.

In a variation thereof, the apparatus may generating a "fresh" baseline 3D surface representation after a selected time of tracking and/or in case of an event, such as restarting a scanning and/or detection of scanning errors and/or false motions beyond a threshold.

In another variation thereof, the apparatus may adjust the weight(s) of the first constraint in dependence of a detected shift between a virtual feature associated to the ROI of the baseline 3D surface representation and the corresponding virtual feature associated to the corresponding ROI of the subsequent 3D surface representation to be subjected to the best-fit registration.

In a further variation thereof, the apparatus may apply one or more further constraint in the determination of a best-fit registration of the subsequent 3D surface representation where a detected shift between a virtual feature associated to the ROI of the baseline 3D surface representation and the corresponding virtual feature associated to the corresponding ROI of the subsequent 3D surface representation to be subjected to the best-fit registration exceeds a threshold.

Figure 10:
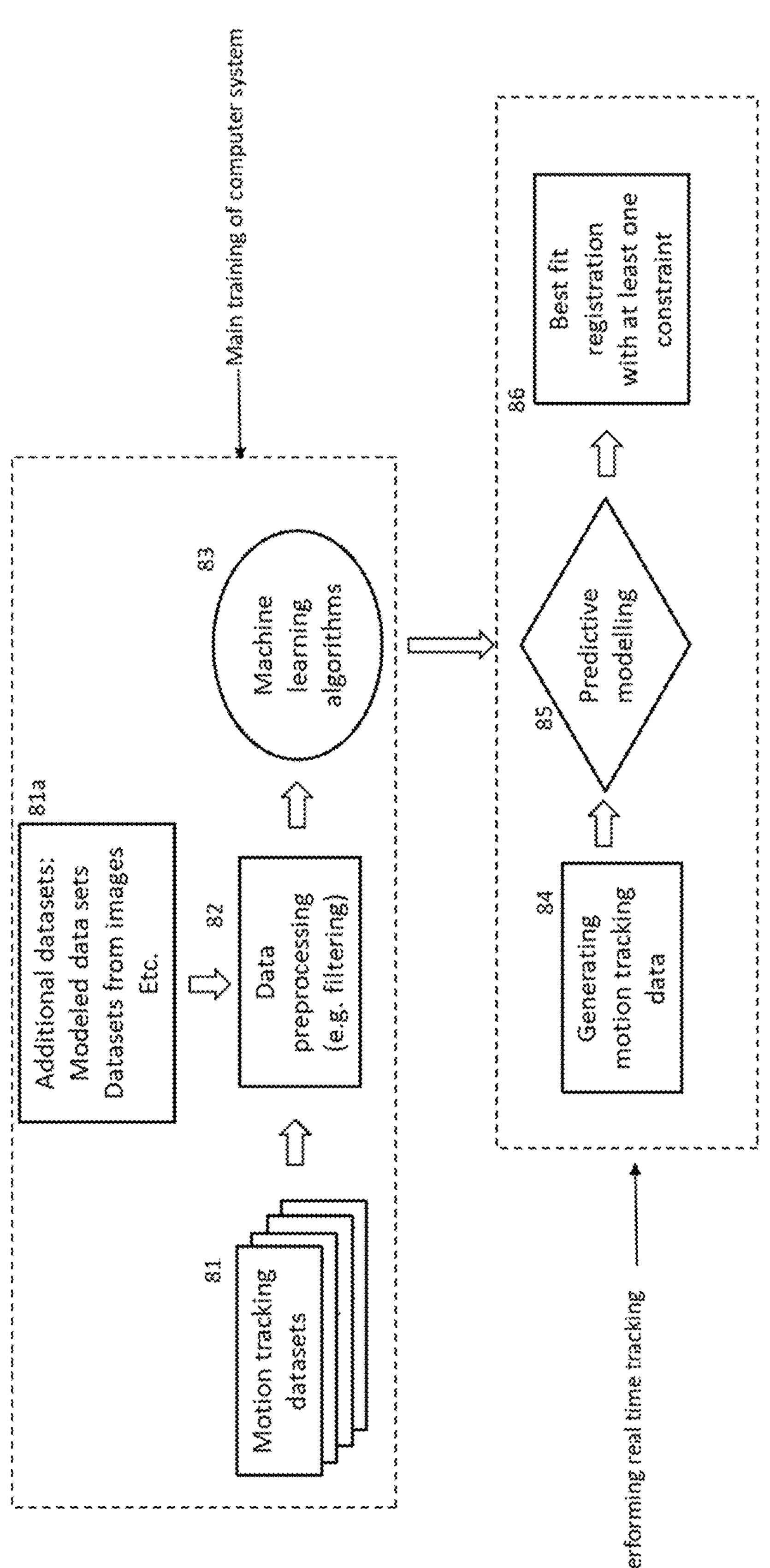
FIG. 10 is a process diagram of an embodiment of training a computer system of the method according to the invention.

FIG. 10 illustrates a method of an embodiment of training a computer system of the method according to the invention.

In step, 81 a plurality of motion datasets are generated, for example using any of the methods as described above. Advantageously, the data sets comprises motion tracking data sets wherein constraint(s) is/are applied preferably involving 6 DOF constraints. The datasets may further include unconstrained datasets.

Alternatively, some or all of these motion data sets are generated using any other constraints as described above or even without applying any constraints.

Each dataset comprises a set of attributes representing the optional constraints (including preferably one or more of weight(s), virtual feature(s), DOF . . . etc.), criterion(s) associated to the scanning procedure and/or criterion(s) associated to the subject.

The criterion may for example comprise one or more of the above described criterions.

In step, 81*a* a plurality of additional datasets are supplied including advantageously modeled datasets, datasets from images and/or any other datasets.

The respective data sets of step 81*a* may advantageously comprise one or more attributes associated to the scanning procedure and/or criterion(s) associated to the subject.

The data sets of steps 81 and/or step 81*a* may be subjected to a filtering process in step 82. The filtering process may advantageously comprise, preferably comprising removing of outlier data, removing data representing anatomical unrealistic motions/position, removing and/or repairing blurred data, removing or suppressing noise, reducing size (e.g. removing irrelevant data portions) and etc.

The data sets are thereafter in step 83 transmitted to a computer system adapted for machine learning and at least one machine learning algorithm is generated by the computer system. The computer system has now been trained and may be applied for use in the method as described herein. The trained computer system may be further refined by subjecting it with training of additional data sets e.g. generated by the use of the computer system.

In step 84, actual tracking data sets are transmitted to the trained computer system. The actual tracking data may be real time tracking data. The actual data sets includes at least a data set representing a baseline 3D surface representation (subsequent data set) of a surface region of the subject at a first point of time (T(0)) and a data set representing a subsequent 3D surface representation of the surface region of the subject at a subsequent point of time (T(s)), The data may be transmitted to the computer system in real time as they are acquired.

Step 85 indicates the processing of the trained computer, wherein the trained computer is using its machine learning algorithms to perform a predictive modelling determining and applying one or core constraints as described above to thereby suppress canning errors and/or false motions. In addition to the actual tracking data sets the computer system may receive and/or acquire (e.g. from a data base) data representing criterion associated to the scanning procedure to be run by the scanner, a criterion associated to the subject and/or a criterion associated to a location and/or body part to be scanned.

Step 86 illustrated the determined best-fit registration with one or more constraints ad determined by the trained computer system preferably in real time. The best-fit registration for each subsequent data set may for example be transmitted to a controller of the scanner and/or to a display unit, such as a screen e.g. displaced as actual motions of the subject located in the scanner.

Figure 11:
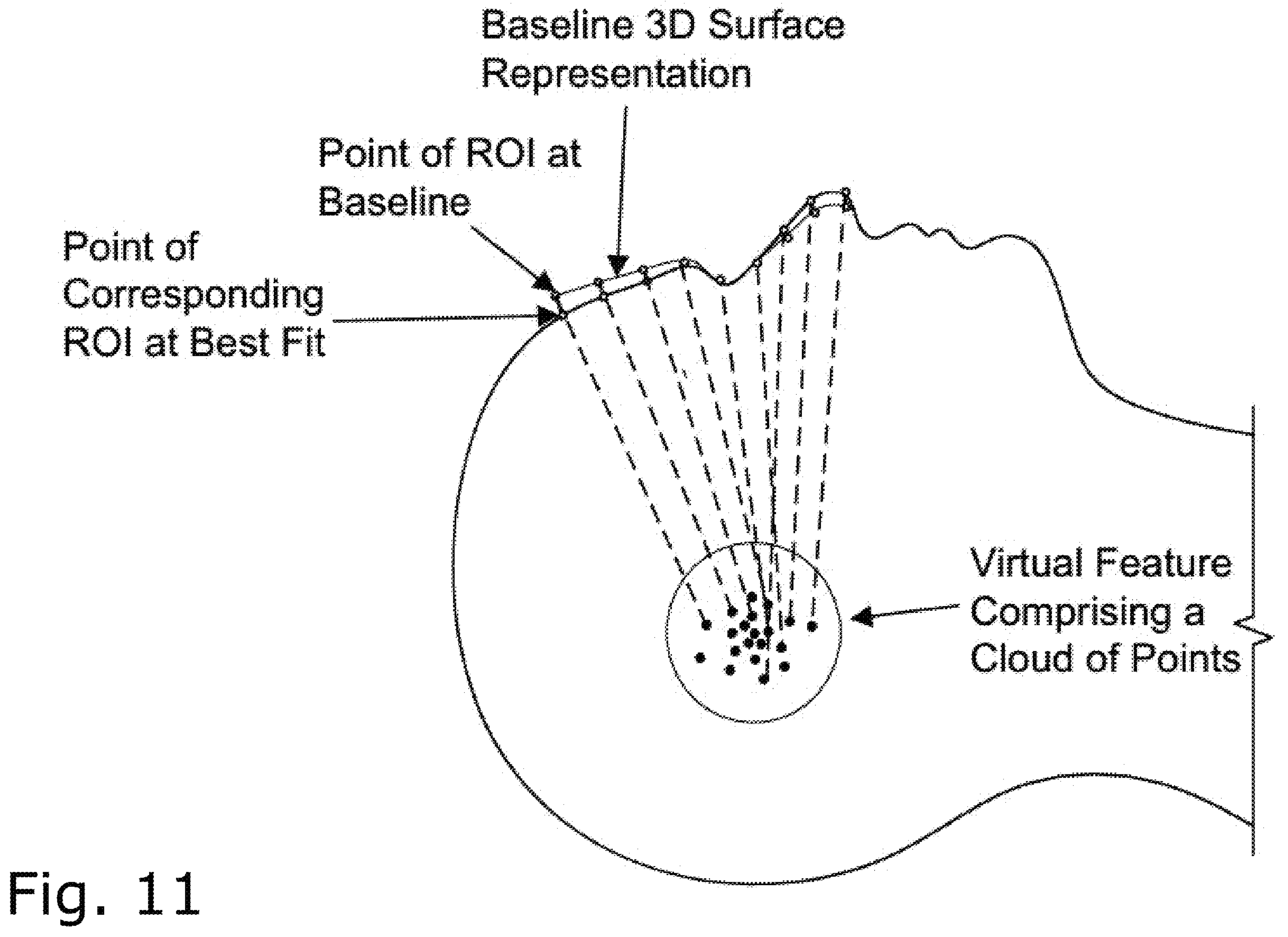
FIG. 11 illustrates a cross sectional side view of an illustration of a body portion in the form of a head in a part of a tracking session.

FIG. 11 illustrates a cross sectional side view of an illustration of a body portion in the form of a head in a part of a tracking session.

The at least one virtual feature is selected to comprise a cloud of points (cloud points) e.g. comprising points at location determined by a Gaussian function around a central location of the head.

A plurality of the points (cloud points) of the cloud of points are associated to a baseline 3D surface representation at respective points (ROI points) of a set of points of the ROI of the baseline 3D surface representation as illustrated with the dotted lines.

At a subsequent point of time, a subsequent 3D surface representation of the surface region is obtained and the individual points (cloud points) of the cloud of points are associated to respective corresponding ROI points (cROI points) of the set of points of the corresponding ROI of the subsequent 3D surface representation of the surface region.

Changes of distances from respective ROI points to respective points of the cloud of points (respective ROI points to respective cloud points) and respective corresponding ROI points of the subsequent 3D surface representation to respective points of the cloud of points (respective cROI points to respective cloud points) are subjected to individual constraints to thereby arrive at the best-fit subsequent 3D surface representation as illustrated with the point of corresponding ROI at best-fit.

We claim:

1. A method of motion tracking of a subject located in a scanner, the method comprising:

generating a baseline 3D surface representation of a surface region of the subject at a first point of time (T(0)), generating a subsequent 3D surface representation of the surface region of the subject at a subsequent point of time (T(s)), determining a best-fit registration of the subsequent 3D surface representation with at least one constraint relative to the baseline 3D surface representation, determining at least one motion tracking parameter, wherein, the constraint comprises a relative restriction to provide a suppression of at least one of a false motion and a detection error, wherein the relative restriction is a function of a difference between respective locations of the baseline 3D surface representation and corresponding respective locations of the subsequent 3D surface representation, wherein said respective locations comprises at least one location of a virtual feature and a corresponding ROI (region of interest) and wherein said constraint comprises a restriction of change of at least one parameter of said at least one virtual feature associated to said corresponding ROI of the best-fit subsequent 3D surface representation relative to the at least one parameter of the at least one virtual feature associated to the ROI of the baseline 3D surface representation.

2. The method of claim 1, wherein determining the best-fit registration comprises selecting said at least one virtual feature and associating said at least one virtual feature to said ROI forming said corresponding ROI and wherein said at least one feature has a spatial location or orientation relative to the corresponding ROI and wherein said at least one parameter comprises said spatial location or orientation relative to the corresponding ROI.

3. The method of claim 2 wherein said at least one parameter comprises a location parameter, an orientation parameter, an extent parameter, a distance parameter or a combination comprising at least one of the mentioned parameters of said at least one virtual feature associated to said ROI.

4. The method of claim 2, wherein said at least one virtual features comprises at least one of a virtual point, a virtual volume, a virtual area, a virtual line, a virtual bone structure and/or any combination comprising one or more of the mentioned virtual features.

5. The method of claim 2, wherein the ROI is a sub-region or a set of sub-regions of the baseline 3D surface representation corresponding to actual sub-region(s) of the surface region or corresponding to actual sub-region(s) of a portion of the subject at least partly correlated with actual sub-region(s) of the surface region.

6. The method of claim 2, wherein the constraint comprises providing that the at least one virtual feature associated to the corresponding ROI of the best-fit registered subsequent 3D surface representation has been transformed compared to what it would have been without the at least one constraint, wherein said transformed virtual feature(s) comprises a transformation of said at least one parameter, wherein the transformation comprises at least one restriction of said at least one parameter.

7. The method of claim 1, wherein the constraint has at least one degree of freedom (DOF) selected from a translation axis and a rotation axis.

8. The method of claim 1, wherein the constraint is an X DOF constraint, wherein X is an integer from 1-6.

9. The method of claim 1, wherein the constraint is associated to at least one weight attribute representing at least one weight value of the constraint.

10. The method of claim 2, wherein the constraint is associated to a set of weight attributes comprising at least 2 weight attributes each having a weight value, wherein the weight value of the respective weight attributes of the set of weight attributes are derived from a modelling of expected movements of the at least one virtual feature associated to the at least one ROI of the baseline 3D surface representation by movement of an anatomical model of a body part of the subject comprising said surface region.

11. The method of claim 10, wherein the value of the respective weight attributes of the set of weight attributes are dynamically adjusted in dependence of the subsequent 3D surface representation of the surface region.

12. The method of claim 2, wherein the at least one virtual feature as associated to the ROI of the baseline 3D surface representation is spatially located at the surface region or at a distance further from the surface region than an acquisition arrangement acquiring reflected light from the surface region for generating the respective surface representations wherein the at least one virtual feature as associated to the ROI of the baseline 3D surface representation is spatially located between the surface region and a bearing supporting the subject.

13. The method of claim 2, wherein the surface region comprises a surface region of a body part of the subject, wherein the virtual feature comprises a virtual point, a virtual line or a virtual bone structure, which at a first point of time is located inside a volume of the body part and wherein the parameter comprises a location parameter, an orientation parameter and/or a distance parameter.

14. A method of motion tracking of a subject located in a scanner, the method comprising:

generating a baseline 3D surface representation of a surface region of the subject at a first point of time (T(0)), generating a subsequent 3D surface representation of the surface region of the subject at a subsequent point of time (T(s))

determining a best-fit registration of the subsequent 3D surface representation with at least one constraint relative to the baseline 3D surface representation, determining at least one motion tracking parameter, wherein, the constraint comprises a relative restriction to provide a suppression of at least one of a false motion and a detection error, wherein the relative restriction is a function of a difference between respective locations of the baseline 3D surface representation and corresponding respective locations of the subsequent 3D surface representation, wherein the method comprises selecting at least one virtual feature and associating said at least one virtual feature to a ROI (region of interest) forming a corresponding ROI of the baseline 3D surface representation, wherein said respective location(s) comprises a location said at least one virtual feature and said corresponding ROI and wherein said constraint comprises a restriction of change of at least one parameter of said at least one virtual feature associated to said corresponding ROI of the best-fit subsequent 3D surface representation relative to the at least one parameter of the at least one virtual feature associated to the ROI of the baseline 3D surface representation, wherein the surface region comprises a surface region of a body part of the subject, wherein the virtual feature comprises a virtual point, a virtual line or a virtual bone structure, which at a first point of time is located inside a volume of the body part and wherein the parameter comprises a location parameter, an orientation parameter and/or a distance parameter, and wherein the surface region comprises a surface region of a body part of the subject, wherein the virtual feature comprises a virtual volume and/or a virtual area, which at the first point of time is located at the surface region and/or at least partly inside the volume of the body part and wherein the parameter comprises a location parameter, an orientation parameter and/or an extent parameter, wherein the method comprises selecting the at least one virtual feature with a feature spatial location at the first point of time T(0), by providing estimated movements of the subject during a scanning section and selecting the at least one virtual feature with the feature spatial location at the first point of time T(0), which is subjected to less parameter changes than other virtual features of the subject and/or to be a virtual feature with the feature spatial location subjected to parameter changes below a preselected level.

15. The method of claim 2, wherein the method comprises selecting a plurality of constraints for one or more virtual features, comprising selecting at least one weight attribute for each of said respective constraints, where the weight of the respective constraints are selected in dependence of the parameter of the constraint and the baseline parameter.

16. A method of motion tracking of a subject located in a scanner, the method comprising:

generating a baseline 3D surface representation of a surface region of the subject at a first point of time (T(0)), generating a subsequent 3D surface representation of the surface region of the subject at a subsequent point of time (T(s)), determining a best-fit registration of the subsequent 3D surface representation with at least one constraint relative to the baseline 3D surface representation, determining at least one motion tracking parameter, wherein, the constraint comprises a relative restriction to provide a suppression of at least one of a false motion and a detection error, wherein the relative restriction is a function of a difference between respective locations of the baseline 3D surface representation and corresponding respective locations of the subsequent 3D surface representation, wherein the method comprises selecting at least one virtual feature and associating said at least one virtual feature to a ROI (region of interest) forming a correlated ROI of the baseline 3D surface representation, wherein said respective location(s) comprises a location said at least one virtual feature and said corresponding ROI and wherein said constraint comprises a restriction of change of at least one parameter of said at least one virtual feature associated to said corresponding ROI of the best-fit subsequent 3D surface representation relative to the at least one parameter of the at least one virtual feature associated to the ROI of the baseline 3D surface representation, wherein the at least one virtual feature as associated to the ROI of the baseline 3D surface representation is spatially located at the surface region or at a distance further from the surface region than an acquisition arrangement acquiring reflected light from the surface region for generating the respective surface representations wherein the at least one virtual feature as associated to the ROI of the baseline 3D surface representation is spatially located between the surface region and a bearing supporting the subject, and wherein the method comprises providing a trained computer comprising a method of training a computer for selecting the at least one virtual feature associated to the ROI of the baseline 3D surface representation, and the at least one constraint using sets of reference data, wherein each reference data set comprises reference data representing previously determined or modelled motions of a reference subject correlated to reference data representing determined or modelled motions of a reference surface region, wherein the reference surface region is a surface of a reference body part of said reference subject.

17. The method of claim 16, wherein the reference data representing previously determined or modelled motions of a reference subject comprises reference data representing changes of a parameter of the at least one reference virtual feature associated to said reference surface region caused by said motions, wherein said at least one reference virtual feature is located at said reference surface region or within a volume of the reference body part.

18. A method of motion tracking of a subject located in a scanner, the method comprising:

generating a baseline 3D surface representation of a surface region of the subject at a first point of time (T(0)), generating a subsequent 3D surface representation of the surface region of the subject at a subsequent point of time (T(s)), determining a best-fit registration of the subsequent 3D surface representation with at least one constraint relative to the baseline 3D surface representation, determining at least one motion tracking parameter, wherein, the constraint comprises a relative restriction to provide a suppression of at least one of a false motion and a detection error, wherein the relative restriction is a function of a difference between respective location(s) of the baseline 3D surface representation and corresponding respective location(s) of the subsequent 3D surface representation, wherein the method comprises selecting at least one virtual feature and associating said at least one virtual feature to a ROI (region of interest) forming a correlated ROI of the baseline 3D surface representation, wherein said respective location(s) comprises a location said at least one virtual feature and said corresponding ROI and wherein said constraint comprises a restriction of change of at least one parameter of said at least one virtual feature associated to said corresponding ROI of the best-fit subsequent 3D surface representation relative to the at least one parameter of the at least one virtual feature associated to the ROI of the baseline 3D surface representation, wherein the surface region is a surface region of a body part comprising a body portion to be scanned, and wherein the at least one virtual feature comprises a cloud of points located inside the body part at locations determined by a Gaussian function around a central location of the body part, wherein the ROI of the baseline 3D surface representation corresponds to a set of locations at the surface region and wherein at least a set of points of the cloud points are associated to the ROI of the baseline 3D surface representation of the best-fit subsequent 3D surface representation relative to the at least one parameter of the at least one virtual feature associated to the ROI of the baseline 3D surface representation.

19. A motion tracking apparatus for motion tracking of a subject located in a scanner, the motion tracking apparatus comprising:

an acquisition arrangement configured for acquiring a 3D surface representation of a surface region of the subject;

a computer system in data communication with said acquisition arrangement for receiving data representing said 3D surface representation, wherein the computer system is configured for receiving data representing a 3D surface representation acquired by said camera arrangement at a first point of time and generating a baseline 3D surface representation of the surface region of the subject;

associating at least one virtual feature to a ROI of the baseline 3D surface representation;

receiving data representing a 3D surface representation acquired by said acquisition arrangement at a subsequent time and generating a subsequent 3D surface representation of the surface region of the subject and determining at least one motion tracking parameter comprising determining a best-fit registration of the subsequent 3D surface representation with a constraint relative to the baseline 3D surface representation, wherein the constraint comprises a restriction of change of at least one parameter of said at least one virtual feature associated to a corresponding ROI of the best-fit subsequent 3D surface representation relative to the at least one parameter of the at least one virtual feature associated to the ROI of the baseline 3D surface representation, and wherein the computer system is configured for carrying out the method of claim 1.

20. A motion tracking apparatus for motion tracking of a subject located in a scanner, the motion tracking apparatus comprising:

an acquisition arrangement configured for acquiring a 3D surface representation of a surface region of the subject;

a computer system in data communication with said acquisition arrangement for receiving data representing said 3D surface representation, wherein the computer system is configured for receiving data representing a 3D surface representation acquired by a camera arrangement at a first point of time and generating a baseline 3D surface representation of the surface region of the subject;

associating at least one virtual feature to a ROI of the baseline 3D surface representation;

receiving data representing a 3D surface representation acquired by said acquisition arrangement at a subsequent time and generating a subsequent 3D surface representation of the surface region of the subject and determining at least one motion tracking parameter comprising determining a best- fit registration of the subsequent 3D surface representation with a constraint relative to the baseline 3D surface representation, wherein the constraint comprises a restriction of change of at least one parameter of said at least one virtual feature associated to a corresponding ROI of the best-fit subsequent 3D surface representation relative to the at least one parameter of the at least one virtual feature associated to the ROI of the baseline 3D surface representation, and wherein the computer system is configured for carrying out the method of claim 1, wherein the motion tracking apparatus comprises a trained computer, and wherein the trained computer has been trained for selecting at least one of a number N of constrains and associated virtual features to be applied, respective baseline parameter(s) of said respectively virtual features, a number X of DOFs of said respective constraint.

21. The motion tracking apparatus of claim 19, wherein the computer system is configured for receiving user instructions and/or acquiring instruction from a database relating to at least one of a criterion associated to the scanning procedure to be run by the scanner, a criterion associated to the subject and/or a criterion associated to a location and/or body part to be scanned and/or at least one of number N of constrains associated virtual feature(s) to be applied, respective baseline parameter(s) of said respectively virtual features, number X of DOFs of said respective constraint and at least one weight attribute associated to said constraints.

* * * * *